United States Patent [19]

Nazarian et al.

[11] Patent Number: 5,813,972
[45] Date of Patent: Sep. 29, 1998

[54] MEDICAL PERFUSION SYSTEM WITH DATA COMMUNICATIONS NETWORK

[75] Inventors: Richard A. Nazarian, Golden Valley; Dirk R. Smith, St. Paul; James R. Watts, Woodbury, all of Minn.; Timothy J. Kriewall, Castle Rock, Colo.; Richard A. Griewski, Canton Township, Mich.

[73] Assignee: Minnesota Mining and Manufacturing Company, St. Paul, Minn.

[21] Appl. No.: 723,504

[22] Filed: Sep. 30, 1996

[51] Int. Cl.⁶ .................................................. A61M 1/00
[52] U.S. Cl. .............................................................. 600/17
[58] Field of Search .................................. 600/17, 16, 18; 607/2, 3

[56] References Cited

U.S. PATENT DOCUMENTS

| | | | |
|---|---|---|---|
| 4,722,224 | 2/1988 | Scheller et al. | 73/599 |
| 5,001,642 | 3/1991 | Botzenhardt et al. | 364/431.12 |
| 5,059,167 | 10/1991 | Lundquist et al. | 600/17 |
| 5,105,441 | 4/1992 | Borst et al. | 375/17 |
| 5,111,460 | 5/1992 | Botzenhardt et al. | 371/29.1 |
| 5,216,674 | 6/1993 | Peter et al. | 371/29.5 |
| 5,222,110 | 6/1993 | Holzinger et al. | 377/44 |
| 5,303,348 | 4/1994 | Botzenhardt et al. | 395/325 |
| 5,341,497 | 8/1994 | Younger | 395/575 |
| 5,357,518 | 10/1994 | Peter | 371/11.2 |
| 5,387,122 | 2/1995 | Goldberger et al. | 439/353 |
| 5,444,626 | 8/1995 | Schenk | 364/431.04 |
| 5,448,180 | 9/1995 | Kienzler et al. | 326/15 |
| 5,448,561 | 9/1995 | Kaiser et al. | 370/85.1 |
| 5,493,515 | 2/1996 | Batchelder et al. | 364/550 |
| 5,499,336 | 3/1996 | Preis et al. | 395/182.02 |
| 5,510,989 | 4/1996 | Zabler et al. | 364/424.05 |
| 5,513,288 | 4/1996 | Mayer | 385/30 |
| 5,524,213 | 6/1996 | Dais et al. | 395/200.17 |
| 5,539,778 | 7/1996 | Kienzler et al. | 375/317 |
| 5,564,108 | 10/1996 | Hunsaker et al. | 395/800 |
| 5,572,658 | 11/1996 | Mohr et al. | 395/182.02 |
| 5,609,770 | 3/1997 | Zimmerman et al. | 210/739 |
| 5,622,429 | 4/1997 | Heinze | 395/200 |
| 5,627,531 | 5/1997 | Posso et al. | 341/22 |

FOREIGN PATENT DOCUMENTS

| | | | |
|---|---|---|---|
| 0 609 688 | 8/1994 | European Pat. Off. | G06F 15/42 |
| 0 690 291 | 3/1996 | European Pat. Off. | |
| 0 745 348 | 12/1996 | European Pat. Off. | A61B 5/00 |
| 0 748 609 | 12/1996 | European Pat. Off. | A61B 5/00 |
| 0 762 815 | 3/1997 | European Pat. Off. | H05K 5/00 |
| 0 768 060 | 4/1997 | European Pat. Off. | A61B 5/215 |
| 24 55 229 | 5/1976 | Germany | A61M 1/03 |

OTHER PUBLICATIONS

Jostra HL20 User's Manual, Jostra AB, Sweden, 120 pages, undated.
Jostra HL20 Technical manual, sep. 9, 1994, 46 pages.

(List continued on next page.)

*Primary Examiner*—William E. Kamm
*Assistant Examiner*—Kennedy J. Schaetzle
*Attorney, Agent, or Firm*—Gary L. Griswold; Stephen W. Bauer; Martin J. Hirsch

[57] ABSTRACT

A medical perfusion system for use in connection with the medical treatment of a patient is provided with a first type of perfusion device in the form of a blood pump adapted to pump blood through a fluid conduit connected to the patient, a second type of perfusion device in the form of a sensor adapted to sense a condition relating to the pumping of blood through the fluid conduit and to generate a sensing signal relating to the condition, and a data communications network for operatively interconnecting the perfusion devices. The perfusion system also includes means for transmitting messages in the form of digital data packets among the perfusion devices over the data communications network and a controller operatively coupled to the perfusion devices via the data communications network, the controller having an input device for accepting pump control commands relating to the blood pump from an operator.

15 Claims, 15 Drawing Sheets

OTHER PUBLICATIONS

Sarns™ 9000 Perfusion System Operators Manual, Sep. 1995, pp. i–v; A–C; 1.1–1.11; 2.1–2.11; 3.1–3.11; 4.1–4.10; 5.1–5.7; 6.1–6.9; 7.1–7.6; 8.1–8.6; 9.1–9.4; 10.1–10.4; 11.1–11.3; 12.1–12.4; 13.1–13.2; 14.1–14.3; 15.1; 16.1–16.4; 17.1–17.14; 18.1–18.6; 19.1–19.19; 20.1–20.56, including Additional insert, 4 sheets; and Index, pp. 21.1–21.4.

3M™Sarns™ Modular Perfusion System 8000 Operators Manual, May 1996, pp. i–v; 1.1–1.22; 2.1–2.14; 3.1–3.10; 4.1–4.10; 5.1–5.2; 6.1–6.2; 7.1–7.5; 8.1–8.4; 9.1–9.9; 10.1–10.68; and Index, pp. 11.1–11.3.

Cobe/Stockert Perfusion System, Technical Handbook, Cobe Laboratories, Inc., Rev. A, pp. 1–1—1–33; 2–1—2–66; 3–1—3–93; 4–1—4–105; and 5–1—5–29, undated (prior art).

S 3 System, Herz–Lungen–Maschine im Modularsystem, Gebrauchsanweisung, Table of Contents, pp. I–XXI; pp. 1–1—1–2; 2–1—2–28; 3–1—3–14; 4–1—4–22; 5–1—5–262; 6–1—6–22; 7–1—7–8; 8–1—8–16; A–1—A–18, undated.

"BOC Puts Ohmeda Health Care Business Up for Sale"; Medical Devices, Diagnostics & Instrumentation Reports The Gray Sheet; vol. 23, No. 30; Jul. 28, 1997.

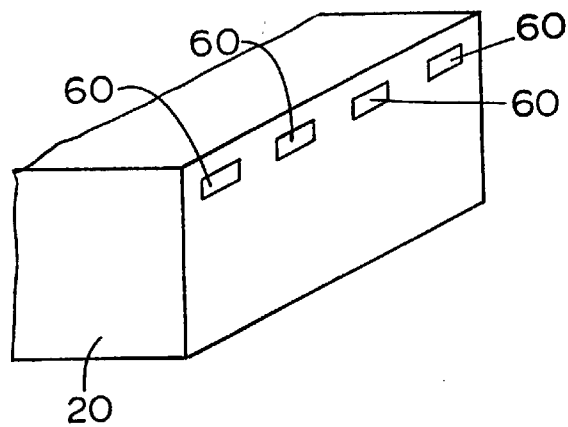
FIG. 2
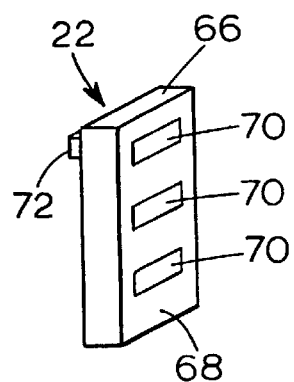
FIG. 3
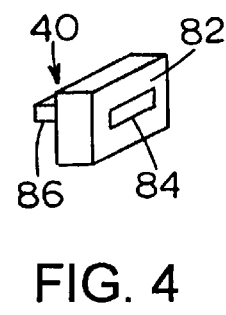
FIG. 4
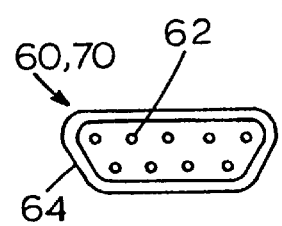
FIG. 5
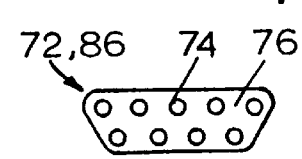
FIG. 6
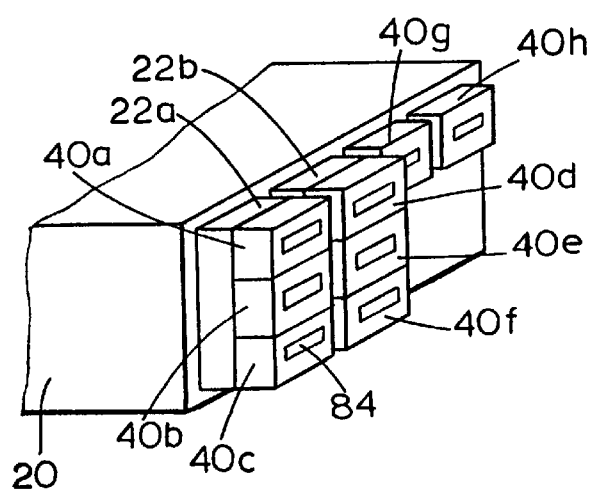
FIG. 8
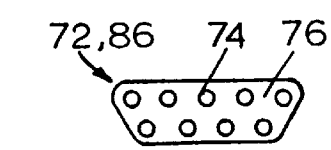
FIG. 7
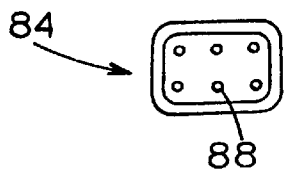

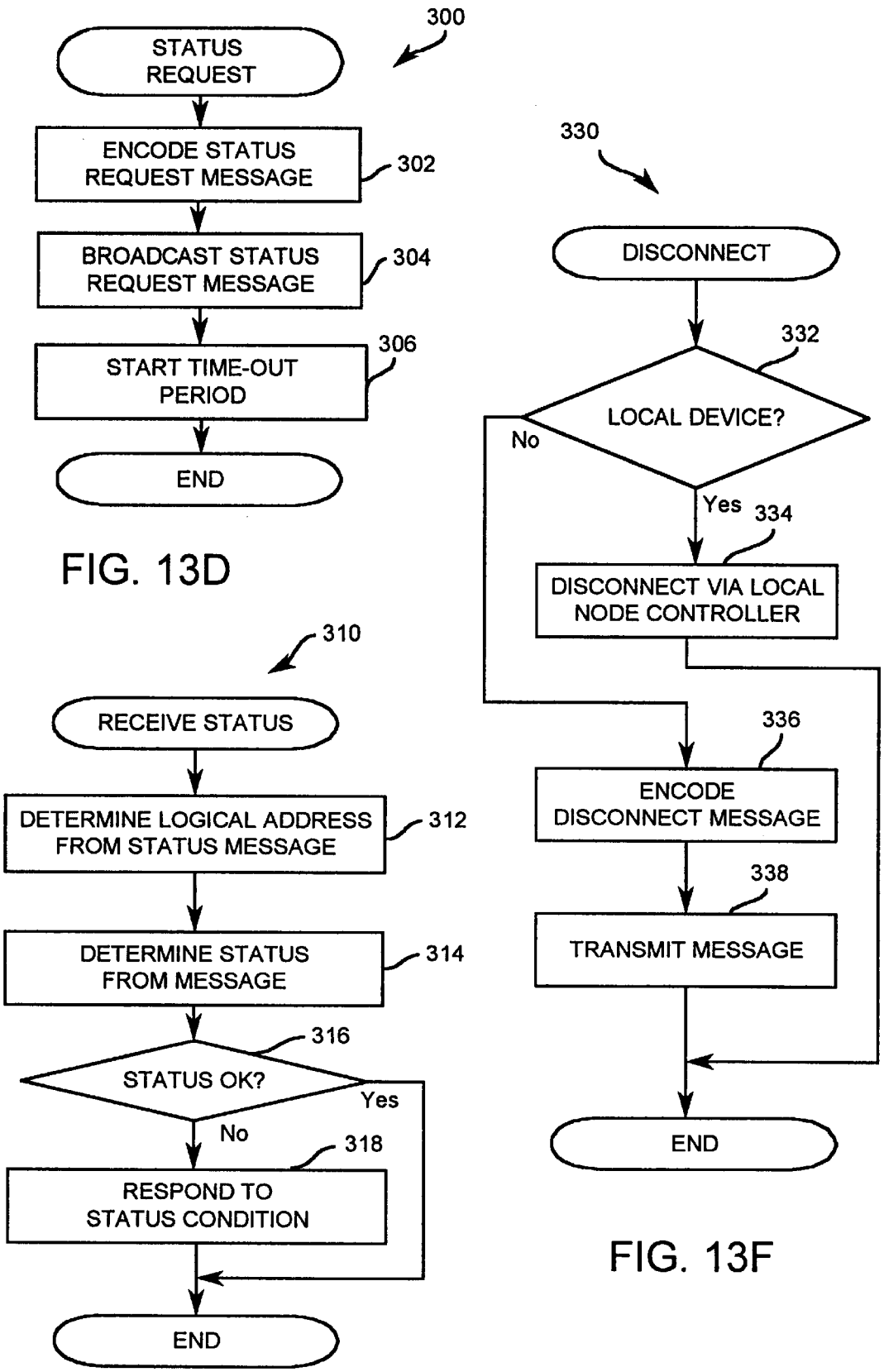

MEDICAL PERFUSION SYSTEM WITH DATA COMMUNICATIONS NETWORK

BACKGROUND OF THE INVENTION

The present invention is directed to a medical perfusion system adapted to handle the selective oxygenation, filtering and recirculation of blood in connection with various medical procedures.

A conventional perfusion system may be used to oxygenate, filter, and/or recirculate the blood of a patient during a medical procedure. Such a perfusion system may have a fluid conduit that removes blood from the patient during the medical procedure, a separate fluid conduit that returns blood to the patient, one or more blood pumps that pump blood through the conduits, and a plurality of sensing devices, such as flow sensors and/or level sensors associated with blood pumps. The perfusion system may also include air embolus sensors, temperature sensors, flow occluders, etc.

Typically, a perfusion system is provided with a configuration specifically designed to be used for a particular purpose. For example, one perfusion system may be specifically designed as a full-function heart/lung machine, while another perfusion system may be specifically designed as a ventricular-assist system. Although it may be possible to convert a perfusion system designed for one purpose to a perfusion system usable for a different purpose, such reconfiguration is generally difficult and/or time-consuming.

SUMMARY OF THE INVENTION

The invention is directed to a medical perfusion system for use in connection with the medical treatment of a patient. The perfusion system includes a first type of perfusion device in the form of a blood pump adapted to pump blood through a fluid conduit connected to the patient, a second type of perfusion device in the form of a sensor adapted to sense a condition relating to the pumping of blood through the fluid conduit and to generate a sensing signal relating to the condition, and a data communications network for operatively interconnecting the perfusion devices. The perfusion system also includes means for transmitting messages in the form of digital data packets among the perfusion devices over the data communications network and a controller operatively coupled to the perfusion devices via the data communications network, the controller having an input device for accepting pump control commands from an operator.

The data communications network may be provided with a plurality of network connectors, each of which has an identical connector configuration, and the perfusion system may include at least two adapter pods, each of which has a common connector adapted to be coupled to one of the network connectors and a device connector adapted to be coupled to one of the perfusion devices. The message transmitting means may include means for generating a message containing a control command for the pump and means for generating a message containing data relating to the sensed condition.

The controller may include a plurality of network connectors, and the data communications network may include a network extender having a network connector adapted to be coupled to one of the network connectors of the controller, a plurality of extender connectors adapted to be connected to the common connectors of the adapter pods, and a data bus electrically interconnecting the network connector of the network extender with each of the extender connectors.

In another aspect, the invention is directed to an adapter pod for use in a medical perfusion system having a data communications network with a plurality of connection points each having a substantially identical network connector. The adapter pod includes a common connector adapted to be connected to one of the network connectors, a device connector adapted to be connected to a perfusion device, and means for generating a message in the form of a digital data packet.

These and other features of the invention will be apparent to those of ordinary skill in the art in view of the detailed description of the preferred embodiments, which is made with reference to the drawings, a brief description of which is provided below.

BRIEF DESCRIPTION OF THE DRAWINGS

FIG. 2 is a perspective view of the main controller shown schematically in FIG. 1;

FIG. 3 is a perspective view of one of the network extenders shown schematically in FIG. 1;

FIG. 4 is a perspective view of one of the adapter pods shown schematically in FIG. 1;

FIGS. 5–7 illustrate a number of connector configurations;

FIG. 8 is a perspective view of the main controller shown schematically in FIG. 1 with two network extenders and eight adapter pods plugged therein;

FIGS. 13A–13H are flowcharts illustrating the operation of the main controller shown in FIG. 1;

DETAILED OF THE PREFERRED EMBODIMENTS

Figure 1:
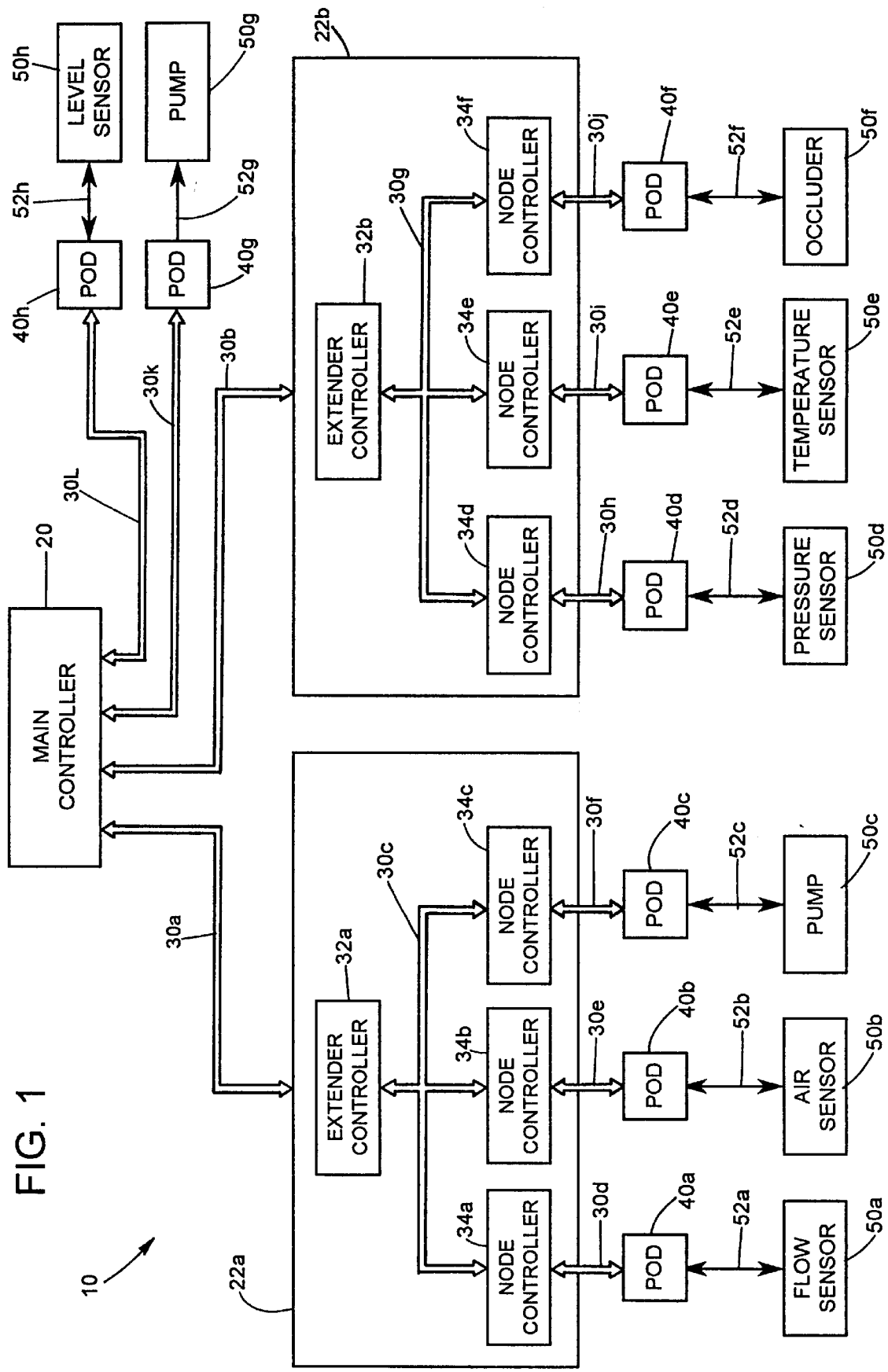
FIG. 1 is a block diagram of a preferred embodiment of a perfusion system in accordance with the invention.

FIG. 1 illustrates a preferred embodiment of a medical perfusion system 10 in accordance with the invention. The perfusion system 10 is adapted to handle the selective oxygenation, filtering and recirculation of blood in connection with a number of different medical procedures. The perfusion system 10 may be placed in a number of different configurations, each of which corresponds to a different medical procedure. For example, the perfusion system 10 may be configured as a full-function heart/lung machine, a ventricular assist system, or a single-pump system that can be used for various purposes, such as to perform blood aspiration or myocardial protection during surgery.

Referring to FIG. 1, the main controller 20 is connected to a network extender 22a via a data/power bus 30a and to a network extender 22b via a data/power bus 30b. The network extender 22a includes an extender controller 32a connected to three node controllers 34a, 34b, 34c via a data/power bus 30c. The node controller 34a is connected via a data/power bus 30d to an adapter pod 40a, which is in turn connected to a perfusion device 50 in the form of a flow sensor 50a via a bidirectional data/power line 52a. The node controller 34b is connected via a data/power bus 30e to an adapter pod 40b, which is connected to an air embolus sensor 50b via a bidirectional line 52b. The node controller 34c is connected via a data/power bus 30f to an adapter pod 40c, which is connected to a blood pump 50c via a bidirectional line 52c.

The network extender 22b includes an extender controller 32b connected to three node controllers 34d, 34e, 34f via a data/power bus 30g. The node controller 34d is connected via a data/power bus 30h to an adapter pod 40d, which is connected to a pressure sensor 50d via a bidirectional line 52d. The node controller 34e is connected via a data/power bus 30i to an adapter pod 40e, which is connected to a temperature sensor 50e via a bidirectional line 52e. The node controller 34f is connected via a data/power bus 30j to an adapter pod 40f, which is connected to a flow occluder 50f via a bidirectional line 52f.

The main controller 20 is operatively coupled to a blood pump 50g via a bidirectional line 52g connected to an adapter pod 40g. The pod 40g is connected to the main controller 20 via a data/power bus 30k. The main controller 20 is operatively coupled to a level sensor 50h via a bidirectional line 52h connected to an adapter pod 40h, which is connected to the main controller 20 via a data/power bus 30l.

As used herein, the term "perfusion device" is a device designed to be used in a medical perfusion system, including but not limited to a blood pump such as a centrifugal or roller pump, a flow sensor, a pressure sensor, a temperature sensor, a level sensor, an air embolus sensor or an occluder.

Mechanical Structure of Network Components

FIG. 2 is a perspective view of a portion of one mechanical embodiment of the main controller 20. Referring to FIG. 2, the main controller 20 has four network connectors 60, which are shown schematically. Each of the network connectors 60 is identical and has the same connector configuration. FIG. 5 illustrates the structure of the connectors 60. As shown in FIG. 5, each connector 60 may be, for example, a standard personal computer connector having nine conductive pins 62 partially surrounded by an asymmetrical metal housing 64.

FIG. 3 is a perspective view of one embodiment of the network extenders 22 shown schematically in FIG. 1. Each network extender 22 has a hexahedral housing 66 with one side 68 on which three connectors 70 are disposed and an opposite side on which a connector 72 is disposed. Each connector 70 is identical to the connectors 60 and has the structure shown in FIG. 5. The connector 72, which is shown in FIG. 6, has nine pin receptacles 74 formed in an asymmetrical housing 76 composed of an insulating material such as plastic. The pin receptacles 74 are located to correspond to the positions of the nine pins 62 of the connector 60. Consequently, the connector 72 has the same connector configuration as the connector 60 and thus can be plugged into the connector 60.

FIG. 4 is a perspective view of the adapter pods 40 shown schematically in FIG. 1. Referring to FIG. 4, each adapter pod 40 has a hexahedral housing with one side 82 on which a connector 84 is disposed and an opposite side on which a connector 86 is disposed. The connector 86 is identical to the connectors 72 described above (and shown in FIG. 6).

The connector 84 is adapted to be connected to a device connector (not shown) that is associated with one of the perfusion devices 50 described above. The connector 84 has a different connector configuration than the connectors 60, 70, 72, 86. One example of the structure of the connector 84 is shown in FIG. 7 to include six conductive pins 88. Since each of the adapter pods 40 is adapted to be connected to a different type of perfusion device 50 (the pumps 50c, 50g may be different types of pumps, such as a roller pump or a centrifugal pump), the connector 84 disposed on each of the adapter pods 40 may have a different connector configuration.

Since the connectors 60 of the main controller 20 and the connectors 70 of the network extenders 22 have the same connector configuration as the connector 86 of the adapter pods 40, it should be noted that any of the adapter pods 40 may be plugged into any of the connectors 60, 70. As a result, any combination of perfusion devices 50 may be connected to the main controller 20.

FIG. 8 illustrates the main controller 20 having the network extenders 22 and the adapter pods 40 connected to it. Each of the adapter pods 40 of FIG. 8 would be connected to a respective one of the perfusion devices 50 shown in FIG. 1 via a respective connector (not shown) attached to the perfusion device 50 by a cable.

Although the form of the network extenders 22 shown in FIGS. 3 and 8 makes the resulting control unit compact, network extenders having different structures could be used. For example, instead of having the connector 72 fixed on the housing 66, the connector 72 could be connected to the housing 66 via a cable. Alternatively, the housing 66 could be eliminated, and the connectors 70, 72 could be interconnected via cables.

Electronics

Figure 9:
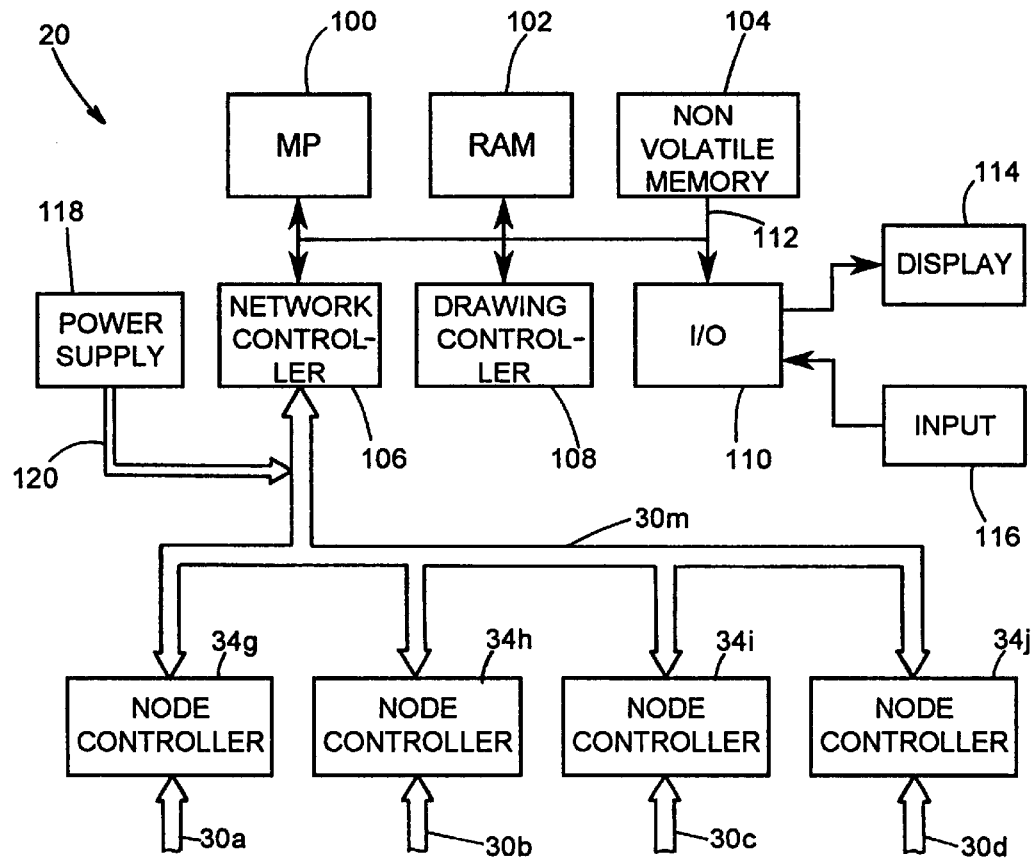
FIG. 9 is a block diagram of the main controller shown schematically in FIG. 1.

FIG. 9 is a block diagram of the main controller 20 shown schematically in FIG. 1. Referring to FIG. 9, the main controller 20 has a microprocessor (MP) 100, a random-access memory (RAM) 102, a nonvolatile memory 104 such as a hard disk or a flash RAM, a network controller 106, a drawing controller 108, and an input/output (I/O) circuit 110, all of which are interconnected by an address/data bus 112. The I/O circuit 110 is connected to a display device 114, such as a CRT or a flat-panel display, and an input device 116, such as a keyboard or electronic mouse or a touch screen on the display device 114.

The main controller 20 also includes a power supply circuit 118 that is connected to an outside source of AC power and which includes an internal transformer (not shown) that generates +5 volt and +24 volt DC power on a pair of electrical power lines relative to a ground line, which lines are schematically designated 120 in FIG. 9. The electrical power and ground lines 120 are provided to each of four node controllers 34g–34j via a data/power bus 30m and to the other node controllers 34 via the other portions of the network bus 30. The data/power bus 30m includes a number of data communication lines which are connected to the network controller 106.

Figure 10:
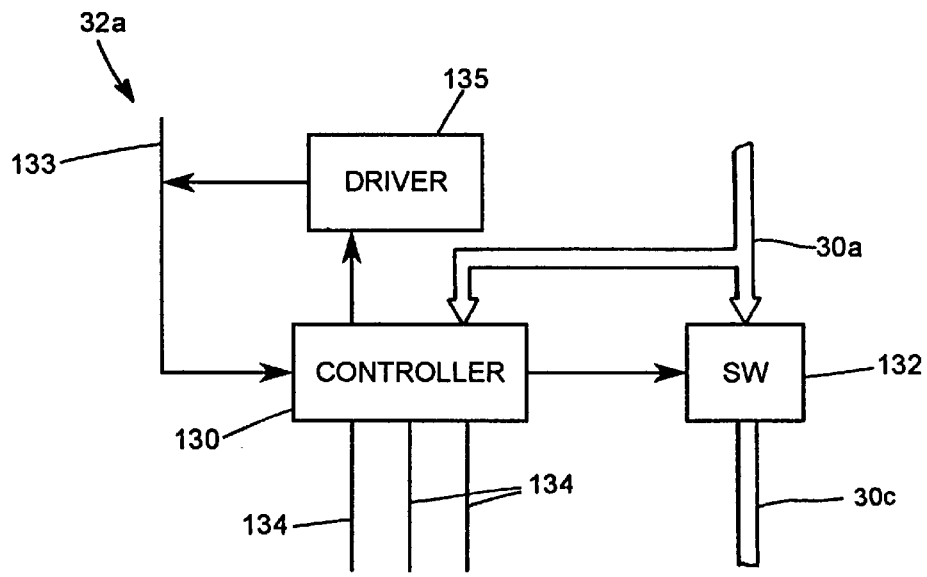
FIG. 10 is a block diagram of one of the extender controllers shown schematically in FIG. 1.

FIG. 10 is a block diagram of the extender controller 32a shown schematically in FIG. 1 (the design of the extender controllers 32a, 32b is the same). Referring to FIG. 10, the extender controller 32a has a controller 130 and a switch 132, both of which are connected to the data/power bus 30*a*. The extender controller 32*a* is connected to its parent node controller 34*g* via a bidirectional signal line 133. As used herein, a "parent" device is a connected device that is closer to the network controller 106 (FIG. 9) of the main controller 20. The node controller 34*g* transmits a unique physical address to the extender controller 32*a* via the line 133, and the extender controller 32*a* includes a driver circuit 135 which is used to periodically transmit a check-in code to the node controller 34*g* via the line 133. The check-in code and the physical address may be the same binary code.

Figure 11:
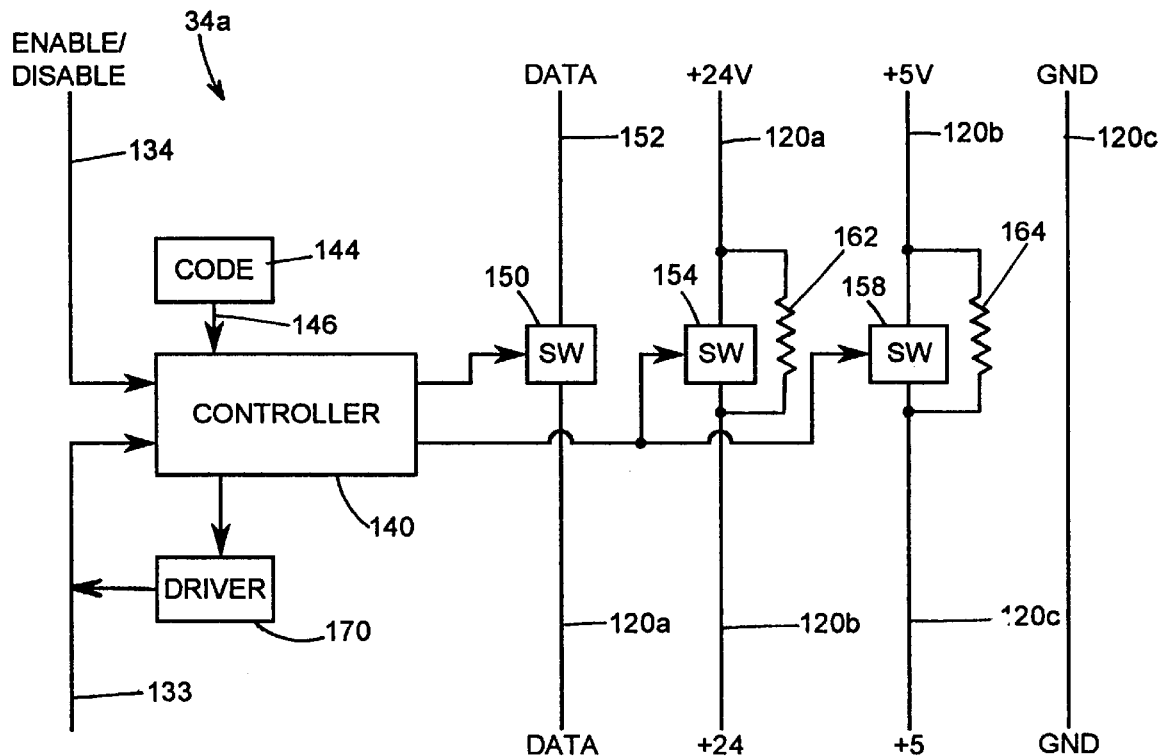
FIG. 11 is a block diagram of one of the node controllers shown schematically in FIG. 1.

FIG. 11 illustrates a block diagram of the node controller 34*a* shown schematically in FIG. 1 (the design of all the node controllers 34 is the same). Referring to FIG. 11, the node controller 34*a* has a controller 140 which receives an enable signal or a disable signal from the extender controller 32*a* via one of the lines 134 and a periodic check-in code from the adapter pod 40*a* via the line 133. The controller 140 is connected to a code generator 144 via a multi-signal line 146. The code generator 144 generates a predetermined multi-bit binary code that uniquely specifies the physical address of the node controller 34*a*. The code generator 144 may be, for example, a number of printed metal circuit lines, one line for each bit of the code, each line being selectively connected either to +5 volts (logic "1") or to ground (logic "0").

The controller 140 selectively operates a switch 150 that either connects or disconnects a data bus 152, which may be composed of two individual data lines, that is part of the data/power buses 30*c*, 30*d* (and the other buses 30 that make up the network). When the switch 150 is open, the data buses 30*c*, 30*d* are disconnected, and when the switch 150 is closed, the buses 30*c*, 30*d* are connected to enable data communications between the adapter pod 40*a* and the other devices connected to the network 30.

The controller 140 also operates a switch 154 that controls whether +24 volt DC power (relative to a ground line 120*c*) on a electrical power line 120*a* is supplied to the adapter pod 40*a* and a switch 158 that controls whether +5 volt DC power on an electrical power line 120*b* is supplied to the adapter pod 40*a*. The electrical power lines 120*a*, 120*b* are part of the data/power buses 30*c*, 30*d* and the other buses 30 that make up the network. A resistor 162 is connected in parallel with the switch 154, and a resistor 164 is connected in parallel with the switch 158. The resistors 162, 164 act as current-limiting resistors which prevent large amounts of current from being drawn from the power lines 120*a*, 120*b* when the switches 154, 158 are open. The controller 140 is connected to a driver circuit 170 which is used to transmit the physical address generated by the code generator 144 to the adapter pod 40*a* via the line 133.

Figure 12:
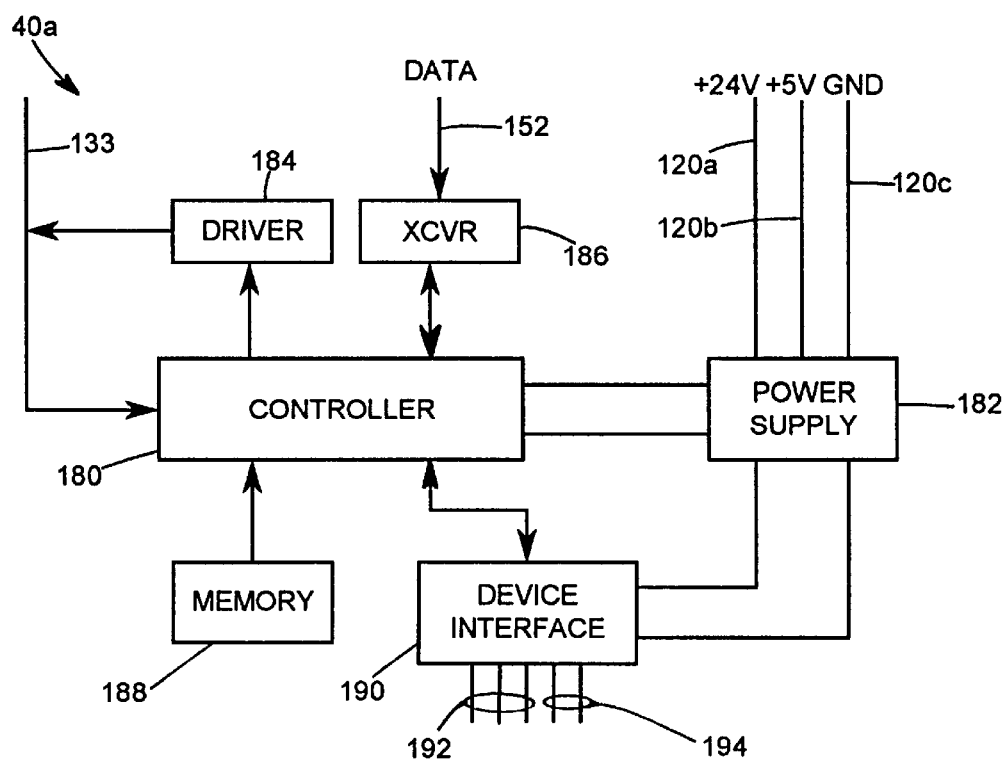
FIG. 12 is a block diagram of one of the adapter pods shown schematically in FIG. 1.

FIG. 12 illustrates a block diagram of the adapter pod 40*a* shown schematically in FIG. 1. Referring to FIG. 12, the adapter pod 40*a* has a controller 180 which is powered by a power supply 182 connected to the electrical power lines 120*a*, 120*b*. The controller 180 may transmit a check-in code on the line 133 via a driver 184. The controller 180 receives network messages from the data bus 152 and transmits messages onto the data bus 152 via a transceiver 186.

The controller 180 is connected to a memory 188 and to a device interface circuit 190. The device interface circuit 190 has a plurality of data lines 192 and a plurality of electrical power lines 194 which are connected to the perfusion device 50*a* via the connector 84 (FIG. 7). The controller 180 causes various types of data signals to be transmitted to the perfusion device 50*a* via the data lines 192.

Depending on the type of perfusion device 50 to which an adapter pod 40 is connected, the signals on the data lines 192 might include, for example, digital or analog signals (e.g. 4–20 ma signals) relating to the control of the perfusion device 50, such as a desired pump speed or mode of operation. The number of data lines 192 used depends on the particular perfusion device 50 to which the adapter pod 40 is connected.

The controller 180 also causes various types of electrical power to be transmitted to the perfusion device 50 via the power lines 194. These types of power include, for example, +5 volt DC power or +24 volt DC power. If power of another voltage level is necessary, the power supply circuit 182 may comprise a DC/DC converter.

Configuration and Display of Perfusion Circuit

Prior to using the perfusion system 10 for a medical procedure, the operator connects the desired perfusion devices 50 to the main controller 20 by physically connecting the desired adapter pods 40 and/or network extenders 22 to the main controller 20, as shown in FIG. 8.

Figure 13A:
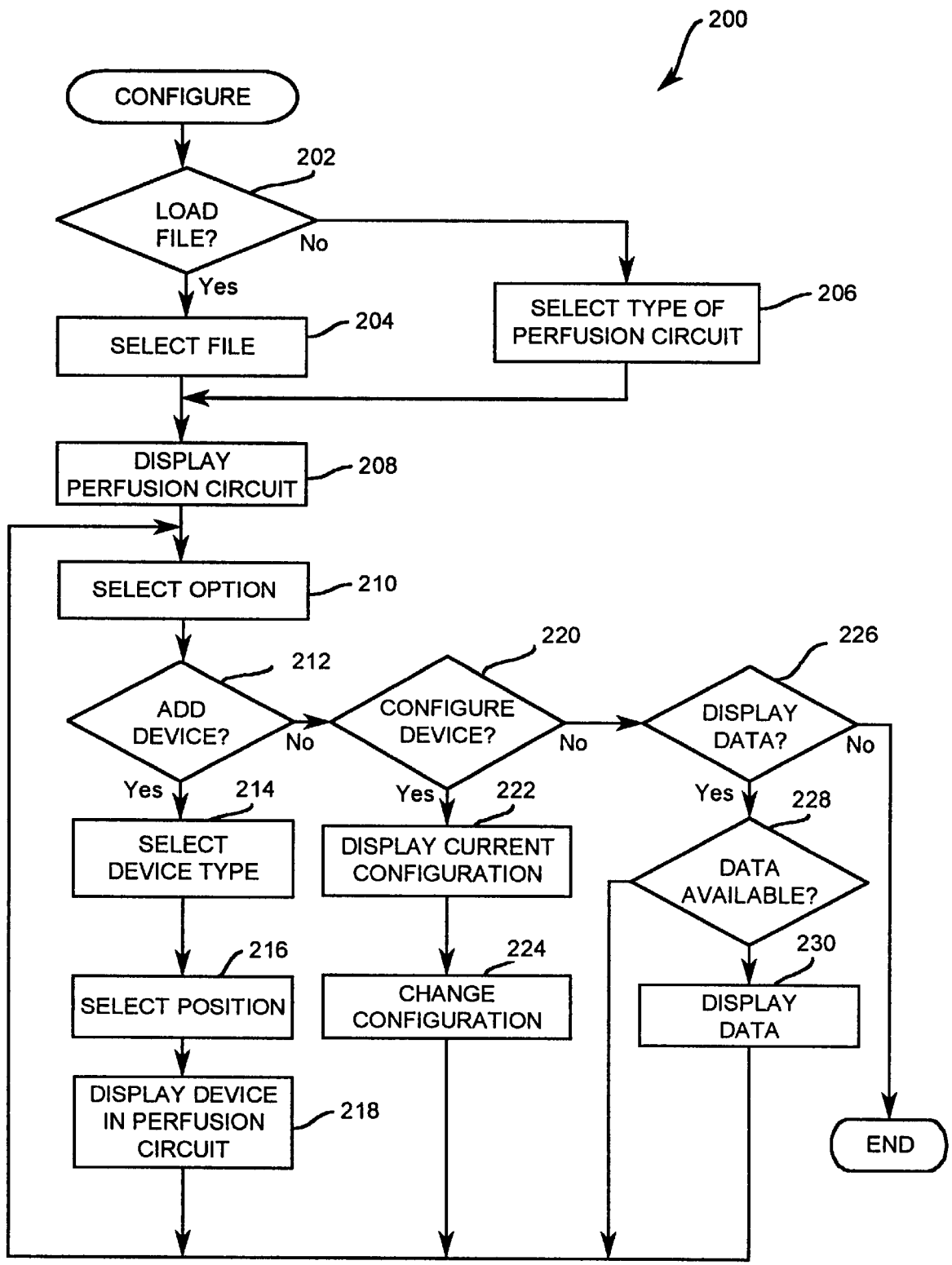

Prior to the commencement of a medical procedure, the perfusion system 10 is configured during a configuration process illustrated in FIG. 13A, which is a flowchart of a configuration computer program routine 200 executed by the main controller 20. Referring to FIG. 13A, at step 202 the program generates a visual prompt to the operator to request whether a previous configuration file should be loaded from the memory 104 of the main controller 20. A configuration file generally includes image data corresponding to an image of a perfusion circuit, which may include an outline of the patient, images of a plurality of fluid conduits connected to the patient, and images of the various perfusion devices 50 used in the system 10. Each perfusion device 50 may be represented by a different image, depending upon the type of perfusion device. For example, pumps may be represented by a pump image, whereas a flow sensor may have a different image.

The configuration file may also include data relating to the perfusion devices 50, such as the manufacturer and model number of the device, the desired operational mode of the device, numeric limits at which an alarm should be triggered, and identification of any associated perfusion device. Two perfusion devices may be "associated" if one device that is used to control a physical process, referred to herein as a control device, is to receive feedback from another perfusion device, referred to herein as a sensing device.

For example, referring to FIG. 1, the pump 50*g* could be controlled based on feedback generated by either the level sensor 50*h* (which would generate a signal indicative of fluid level within a fluid reservoir) or the flow sensor 50*a*. In the former case, the pump 50*g* could be controlled to maintain a predetermined level of fluid within the reservoir, and in the latter case the pump 50*g* could be controlled to maintain a predetermined flow through the conduit. Any type of conventional feedback control could be used, such as proportional-integral (PI) or proportional-integral-derivative (PID) control. Where it is desired to control the pump 50*g* based on the output of the level sensor 50*h*, the association of the pump 50*g* with the level sensor 50*h* would be stored in the configuration file.

Referring to FIG. 13A, if the operator requested the loading of a configuration file at step 202, the program branches to step 204 where the operator is prompted to select one of those configuration files. If the operator did not want to retrieve a previously stored configuration file, the program branches to step 206, where the operator selects one of a predetermined number of types of perfusion circuit images. Each perfusion circuit image could correspond to the perfusion circuit that would be utilized for a different medical procedure. Two different types of perfusion circuit images are illustrated in FIGS. 14A, 14B described below.

At step 208, either the perfusion circuit image corresponding to the configuration file selected at step 204 or the perfusion circuit image selected at step 206 is displayed on the display 114. A pair of exemplary perfusion circuit images that may be displayed on the display 114 are illustrated in FIGS. 14A and 14B.

Figure 14A:
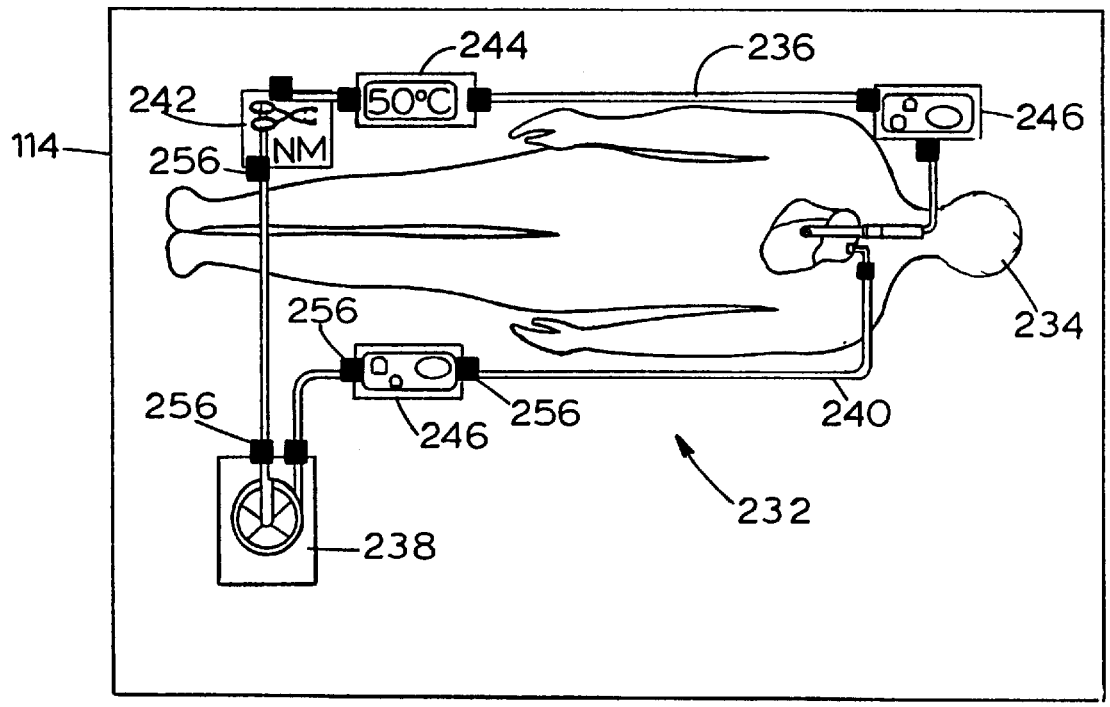
FIGS. 14A–14B are exemplary illustrations of a pair of perfusion circuit images generated on the display device of FIG. 9 during operation of the perfusion system.

Referring to FIG. 14A, an image 232 of a perfusion circuit corresponding to a left ventricle assist device (LVAD)) configuration is shown. The perfusion circuit image 232 includes a patient image 234, an image 236 of a fluid conduit which removes blood from the left ventricle of the patient, an image 238 of a pump, an image 240 of a fluid conduit which returns blood to the aorta of the patient, an image 242 of a flow occluder, an image 244 of a temperature sensor, and a pair of images 246 of an air embolus sensor.

Figure 14B:
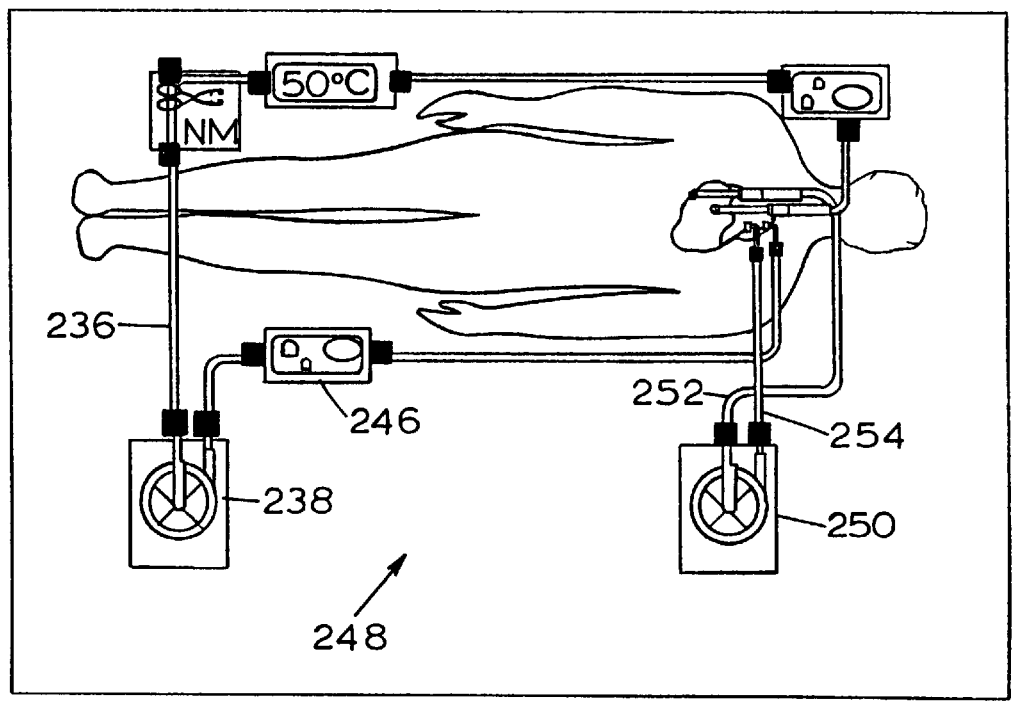

Referring to FIG. 14B, an image 248 of a perfusion circuit corresponding to a bi-ventricular assist device (Bi-VAD) configuration is shown. The perfusion circuit image 248 includes all of the images shown in FIG. 14A, as well as an image 250 of a second blood pump, an image 252 of a conduit which removes blood from right ventricle of the patient, and an image 254 of a conduit that returns blood to the pulmonary artery of the patient. Each of the perfusion circuit images illustrated in FIGS. 14A, 14B could be pre-stored in the memory 104 of the main controller 20, in addition to other types of perfusion circuit images.

At step 210, the operator may select one of a number of configuration options to change the configuration of the perfusion system 10. If the operator selects the option of adding a perfusion device 50 as determined at step 212, the program branches to step 214 where the operator is prompted to select a type of perfusion device 50, such as a pump or a flow sensor, to add to the perfusion circuit image displayed on the display 114.

At step 216, the operator selects the position at which an image of the newly selected perfusion device 50 will be displayed. This position could be specified by the operator via an electronic mouse, and the displayed perfusion circuit image could include a number of possible connection points 256 (FIG. 14A) at which the perfusion device 50 could be connected. The possible connection points 256 could be highlighted, such as by placing them in a bold color or making them blink on and off, so that the possible connection points 256 are readily apparent to the operator. After the operator selects the position, at step 218, an image of the perfusion device is displayed in the perfusion circuit image at that position.

If the operator selected the option of configuring one of the perfusion devices as determined at step 220, the program branches to step 222 where the current configuration of the perfusion device 50 is displayed next to the image of the device in the perfusion circuit. As noted above, the current configuration could include the mode of operation of the perfusion device, alarm limits for the device, any associated perfusion devices, etc. At step 224, the operator may change or add to the current configuration.

If the operator selected the option of displaying data for the perfusion devices as determined at step 226, the program branches to step 228 where it checks to determine whether there is data available to display. Such data could include, for example, the manufacturers and model numbers of the perfusion devices. If there is data available as determined at step 228, the program branches to step 230 where the data is displayed next to the perfusion devices in the perfusion circuit.

Connecting Perfusion Devices

Figure 13B:
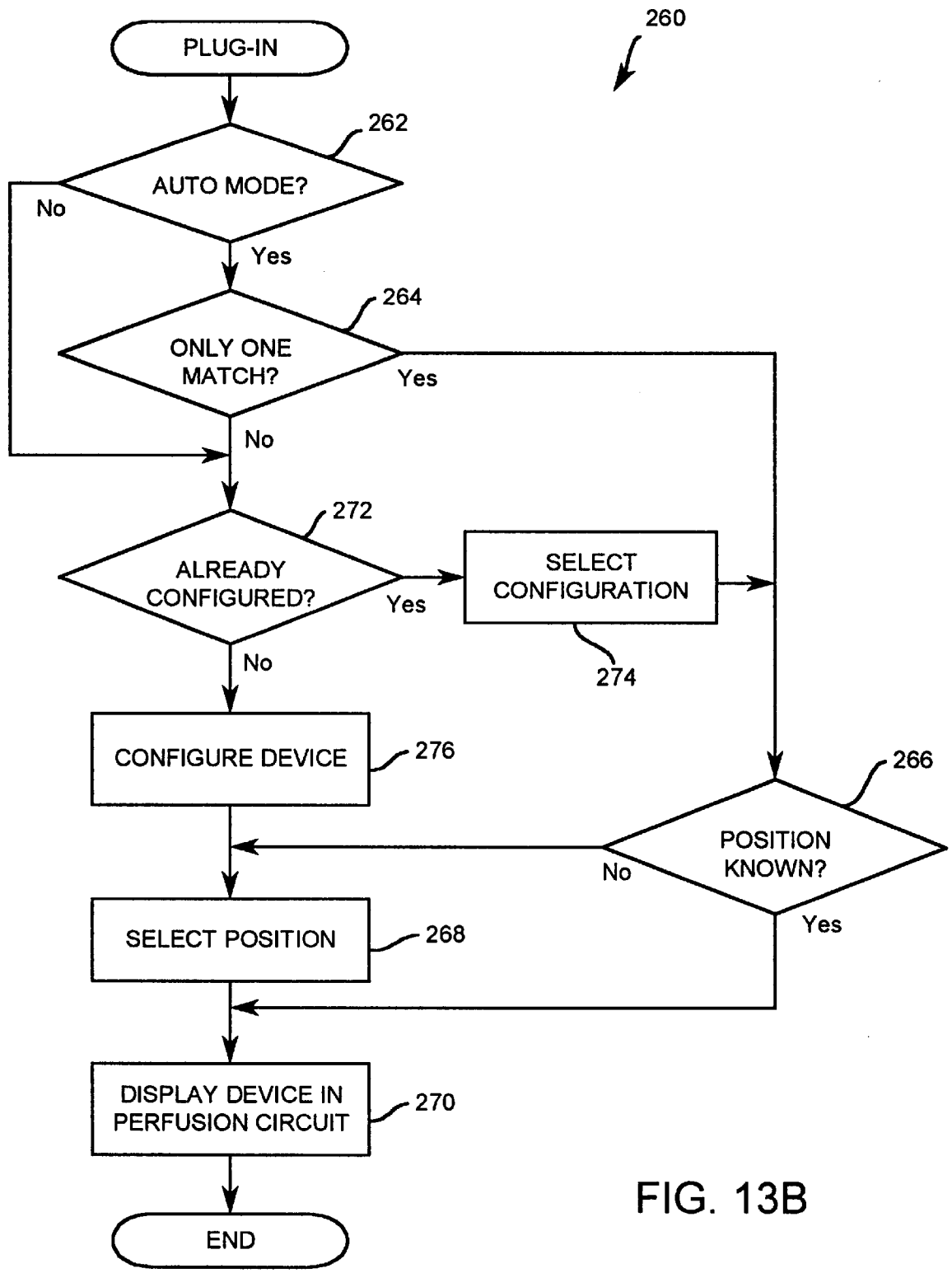

The main controller 20 may utilize a plug-in procedure to accommodate perfusion devices 50 that are subsequently connected to the perfusion system 10. FIG. 13B is a flowchart of a plug-in routine 260 performed by the main controller 20. During the plug-in routine, the main controller 20 may operate in an automatic match mode in which it can match a previously entered device configuration with a perfusion device that is subsequently connected to the main controller 20. For example, a operator may configure a centrifugal blood pump (not yet connected to the main controller 20) to operate in a continuous mode to continuously pump a predetermined flow. When the blood pump is subsequently connected to the controller 20, the controller 20 will then automatically match the previously stored pump configuration with the pump.

Referring to FIG. 13B, at step 262, if the main controller 20 is in the automatic match mode, the program branches to step 264 where it determines whether there is only one possible match between the perfusion device just connected and the previously stored device configurations. This would be the case where there is only one previously stored configuration for a pump and where the device that was just connected to the main controller 20 was a pump.

If there was only one possible match as determined at step 264, the program branches to step 266 where it determines whether the position at which the device is to be displayed in the perfusion circuit image is known. This position could be included in the previously stored configuration for the device. If the position is not known, the program branches to step 268 where the operator is prompted to select a position, and then the program branches to step 270 where an image of the newly connected perfusion device is displayed in the perfusion circuit image. If the position of the device as determined at step 266 was known, the program skips step 268 and branches directly to step 270.

If the main controller 20 was not in the automatic match mode, as determined at step 262, or if there was more than one possible match, as determined at step 264, the program branches to step 272. If the newly connected device has already been configured, the program branches to step 274 where the operator is prompted to select the proper configuration from a plurality of prestored configurations. If the device is not already configured, the program branches to step 276 where the operator enters the desired configuration parameters for the device. The program then performs steps 268 and 270 described above.

Network Communications

The network controller 106 (FIG. 2) in the main controller 20, which may be a conventional network controller such as a CAN Version 2.0B, oversees the data flow on the network buses 30, each of which includes the data bus 152 (which may be composed of two wires) on which digital data packets are transmitted and received. The data packets may have a conventional format composed of the following data fields: 1) a start-of-frame (SOF) field; 2) an arbitration field; 3) a control field; 4) a variable-length data field; 5) an error detection/correction field, such as a cyclic-redundancycheck (CRC) field; 6) an acknowledgement (ACK) field; and 7) an end-of-frame (EOF) field.

The arbitration field, which may be a 29-bit field, is used to determine the priority of the data packets broadcast over the network bus 30. The priority is based on the overall numeric value of the arbitration field of the data packets. In the event of a conflict in the transmission of two data packets, the data packet having the arbitration field with a lower numeric value takes priority. The arbitration fields, which contain a message identification (ID) code specifying the type of message, of a number of different data packet types that may be used are listed below.

| Type | Message ID (MSB to LSB) | | | |
|------|-------|----------|----------|----------|
| A | 00000 | 00000000 | cccccccc | cccccccc |
| B | 00000 | 00000001 | cccccccc | cccccccc |
| C | 00000 | 00000010 | aaaaaaaa | ssssssss |
| D | 00000 | 00000100 | cccccccc | ssssssss |
| E | 00001 | cccccccc | cccccccc | dddddddd |
| F | 00010 | cccccccc | cccccccc | ssssssss |
| G | 10000 | ccacccccc | dddddddd | dddddddd |
| H | 10001 | cccccccc | ssssssss | ssssssss |
| I | 11111 | 11111111 | 11111111 | 11111111 |

In the above table, the message types are listed from highest priority (at the top) to lowest priority (at the bottom). The type A message corresponds to a control message broadcast by the main controller 20 to all devices attached to the network data buses. The data fields "cccccccc cccccccc" are used to specify the type of message. The type B message corresponds to a message broadcast by the main controller 20 to the extender controllers 32. The data fields "cccccccc cccccccc" are used to specify the type of message.

The type C message corresponds to an alarm or safety message, with the data field "aaaaaaaa" specifying an alarm type and the data field "ssssssss" specifying the logical address of the device which generated the alarm message. The type D message corresponds to a servo message generated by a sensing device, such as a flow sensor. The data field "cccccccc" specifies the type of sensed parameter, e.g. flow, and the data field "ssssssss" specifies the logical address of the sensor that generated the sensed parameter.

The type E message corresponds to a general message having a data field "cccccccc cccccccc" which specifies the type of message and a data field "dddddddd" which specifies the logical address of the intended destination of the message. The type F message corresponds to a general message having a data field "cccccccc cccccccc" which specifies the type of message and a data field "ssssssss" which specifies the logical address of the source of the message.

The type G message corresponds to a general message having a data field "cccccccc" which specifies the type of message and a data field "dddddddd dddddddd" which specifies the physical address of the intended destination of the message. The type H message corresponds to a general message having a data field "cccccccc" which specifies the type of message and a data field "ssssssss ssssssss" which specifies the physical address of the source of the message. The type I message (which is all logical "1"s) corresponds to a status request from the main controller 20 that is periodically broadcast to all devices connected to the network data buses.

Some of the message types described above are transmitted without any data fields. For example, the status request message from the main controller 20 would not have a data field. Other messages would include data fields. For example, the servo message (type D above) would include a data field which specified the numeric value of the sensed condition, such as a flow reading of 0.257 liters per minute.

The main controller 20, the extender controllers 32, and the adapter pods 40 may include conventional electronics for checking the accuracy of received messages via the CRC field, requesting retransmission of messages that were not accurately received, and for transmitting acknowledgement messages in response to the receipt of accurately received messages.

The messages described above may be transmitted or broadcast to all the devices connected to the network 30. Each device, such as a pod 40 or an extender controller 32, can discriminate by receiving only certain messages that are broadcast. For example, this discrimination could be accomplished by accessing a message-discrimination memory in the receiving device which stores the logical addresses of all the other devices in which the receiving device is interested.

For example, if the receiving device is the adapter pod 40c connected to the blood pump 50c which controls the flow of blood through a conduit based on receiving a feedback signal from the flow sensor 50a, the message-discrimination memory of the pod 40c would include the logical address of the flow sensor 50a, so that the pod 40c would receive any message generated by the pod 40a connected to the flow sensor 50a.

The message-discrimination memory would include logical address of the main controller 20, and could include the logical addresses of a number of other pods 40. Consequently, it should be noted that it is not necessary that messages broadcast over the network 30 include a specific destination address (although a destination address may be included).

The pods 40 and extender controllers 32 could also discriminate messages based on the type of message instead of the identity of the sender. For example, a pod 40 could receive all status-request messages and configuration messages (described below). The message identification codes for such messages could also be stored in the message-discrimination memory.

Before use of the perfusion system 10 for a medical procedure, and after all the perfusion devices 50 are configured as described above, data packets containing configuration messages are transmitted to all the pods 40 connected to the network 30. The configuration messages include all the necessary configuration data described above. For example, for a blood pump, the configuration data would include the operational mode of the pump, the desired flow rate of the pump, etc. If any configuration messages which include device association data (e.g. the sensor which a blood pump should receive feedback from) were received by a pod 40, the message-discrimination memory would be updated with the logical address of the associated device.

Connecting Pods to the Network

In order for them to communicate with the main controller 20 via the network data/power buses 30, the adapter pods 40 must be granted permission to connect to the network 30. This connection is initiated with a startup-request message transmitted to the main controller 20 by the adapter pod 40 for which the network connection is to be made. The startup-request message includes a first code identifying the type of perfusion device 50 connected to the pod 40 requesting to be connected and a second code identifying the physical address (specified by the code generator 144 of FIG. 11) of the pod 40 requesting to be connected.

Figure 13C:
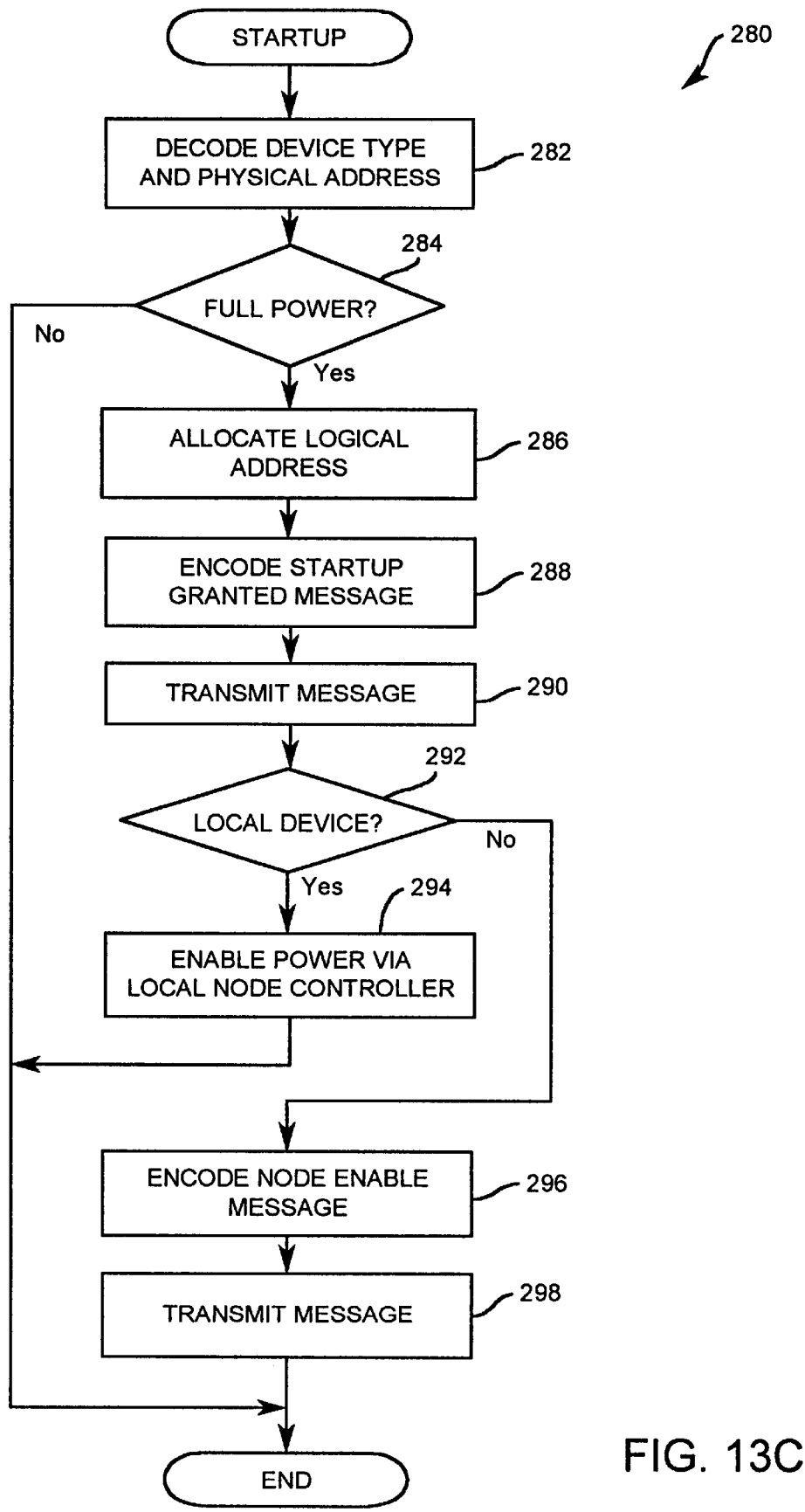

FIG. 13C is a flowchart of a startup routine 280 that is performed by the main controller 20 in response to the receipt of a startup-request message from an adapter pod 40. The startup routine 280 may be an interrupt service routine which is invoked in response to an interrupt generated upon the receipt of a startup-request message by the main controller 20. Referring to FIG. 13C, at step 282, the startup message received by the main controller 20 is decoded to determine the type of the perfusion device 50 attached to the pod 40 requesting to be connected and to determine the physical address of the pod 40.

At step 284, the program determines whether full power should be granted to the requesting pod 40. As described above, electrical power to run the perfusion devices 50 is provided to the pods 40 via the network 30 from a power supply 118 (FIG. 9) in the main controller 20. Since the power available from the power supply 118 may be limited, the main controller 20 may be programmed to allow only a certain number of perfusion devices 50 to be connected to the network 30, or alternatively, to allow only certain numbers of specific types of perfusion devices 50 to be connected. For example, since control devices such blood pumps typically draw more power than sensing devices, the main controller 20 may be provided with an upper limit on the number of control devices that can be connected to the network 30.

At step 284, the decision whether to grant full power could be made by comparing the number of perfusion devices 50 already connected to the network 30 with the maximum number that can be connected to determine whether the connection of an additional device 50 will cause the maximum to be exceeded. Alternatively, if the device requesting connection is a control device, then the number of control devices already connected could be compared with the maximum number of control-type perfusion devices that can be connected. If it is determined that full power should not be granted, the program simply ends.

If it is determined that full power should be granted, steps 286–298 are performed to generate and transmit a startup granted message that will cause the pod 40 associated with the perfusion device 50 to be connected to the network 30. In particular, at step 286, a unique logical address is allocated to the newly connected pod 40. For example, where the capacity of the network 30 is sixteen devices, the logical address may be a four-bit binary code. At step 288, a startup-granted message which includes the logical address is encoded, and at step 290 the startup-granted message is transmitted over the network 30.

At step 292, if the pod 40 which requested startup is local to the main controller 20 (i.e. if it is one of the pods 40g or 40h directly connected to the main controller 20 without a network extender 22), full power to the pod 40 is enabled via the local node controller (i.e. one of the node controllers 34i–34j of FIG. 9) connected to the perfusion device 50. Referring to FIG. 11, this is accomplished by sending an enable signal on the line 134, which will cause the controller 140 to close the switches 150, 154, 158 so that full power is supplied on the power lines 120a, 120b and so that the adapter pod 40 is connected to the data bus 152.

Referring to FIG. 13C, if the perfusion device was not a local device as determined at step 292, the program branches to step 296 where a connect message which includes the physical address of the node controller 34 associated with the pod 40 requesting startup is encoded, and then to step 298 where the connect message is transmitted over the network 30. As described below, when the extender controllers 32 receive the connect message, they decode it to determine the physical address, and the extender controller 32 connected to the node controller 34 having that physical address (i.e. the node controller 34 associated with the requesting pod 40) turns on full power by transmitting an enable signal on the line 134 connected to that node controller.

Status Requests

During operation of the perfusion system 10, to ensure that all devices connected to the network 30 are property functioning and are receiving messages broadcast over the network 30, the main controller 20 periodically transmits a status-request message to all extender controllers 32 and adapter pods 40 on the network 30. Each extender controller 32 and adapter pod 40 must respond to the status request within a predetermined period of time. Any extender controller 32 or pod 40 that fails to respond to the status request within that time period is disconnected from the network 30, and a corresponding alarm message is generated on the visual display 114 to warn the operator of such event.

FIG. 13D is a flowchart of a status-request routine 300 periodically performed by the main controller 20. Referring to FIG. 13D, at step 302 a status-request message is encoded, and at step 304 the message is broadcast to all extender controllers 32 and adapter pods 40 connected to the network 30. As described above, the status-request message may simply be all logical "1"s in the arbitration of the data packet. At step 306, a predetermined time-out period within which all extender controllers 32 and pods 40 must respond to the status request message is started.

Upon receiving the status-request message, each extender controller 32 and adapter pod 40 encodes a status message with its logical address and its status, and then broadcasts the status message to the main controller 20 over the network 30.

FIG. 13E is a flowchart of a receive status routine 310 that is performed by the main controller 20 upon receipt of a status message transmitted to it in response to the status-request message previously transmitted by the routine 300. Referring to FIG. 13E, at step 312 the logical address of the responding extender controller 32 or adapter pod 40 is determined from the status message, and at step 314 the status of the device 32 or 40 is determined from the message. The status may be specified by a number of different binary status codes. At step 316, if the status of the device 32 or 40 is okay, the program simply ends. However, if the status is not okay, the program branches to step 318 where it responds to a status condition identified by the status code. If the condition is relatively minor, the main controller 20 may simply generate a warning on the visual display 114 of the perfusion system 10. If the condition is serious enough, the main controller 20 may disconnect the device 32 or 40 from the network 30.

FIG. 13F is a flowchart of a disconnect routine 330 that causes an extender controller 32 or an adapter pod 40 to be disconnected from the network 30. The disconnect routine 330 is performed by the main controller 20 in response to either: 1) the failure of a device 32 or 40 to transmit a status message to the main controller 20 within the timeout period described above or 2) a serious malfunction of a device 32 or 40 as determined at step 318 of FIG. 13E.

Referring to FIG. 13F, at step 332, if the device 32 or 40 to be disconnected is local to the main controller 20, the program branches to step 334 where that device 32 or 40 is disconnected by the node controller 34g, 34h, 34i, or 34j in the main controller 20 that is connected to that device 32 or 40. Referring to FIG. 11, the disconnection is accomplished by transmitting a disable signal on the line 134, which will cause the controller 140 to open the switches 150, 154, 158 so that the data bus 152 and the power lines 120a, 120b are disconnected.

At step 332, if the device to be disconnected is not local to the main controller 20, the program branches to step 336 where a disconnect message which includes the physical address of the node controller 34 of the device 32 or 40 to be disconnected is encoded, and then to step 338 where the disconnect message is transmitted over the network 30.

If the device to be disconnected is a pod 40 connected to an extender controller 32 via a node controller 34, when that extender controller 32 receives the disconnect message, it decodes it to determine the physical address of the pod 40 to be disconnected, and the node controller 34 associated with that pod 40 disconnects the pod 40 by transmitting a disable signal on the line 134 connected to that node controller 34.

Operator Commands Input to Main Controller

Figure 13G:
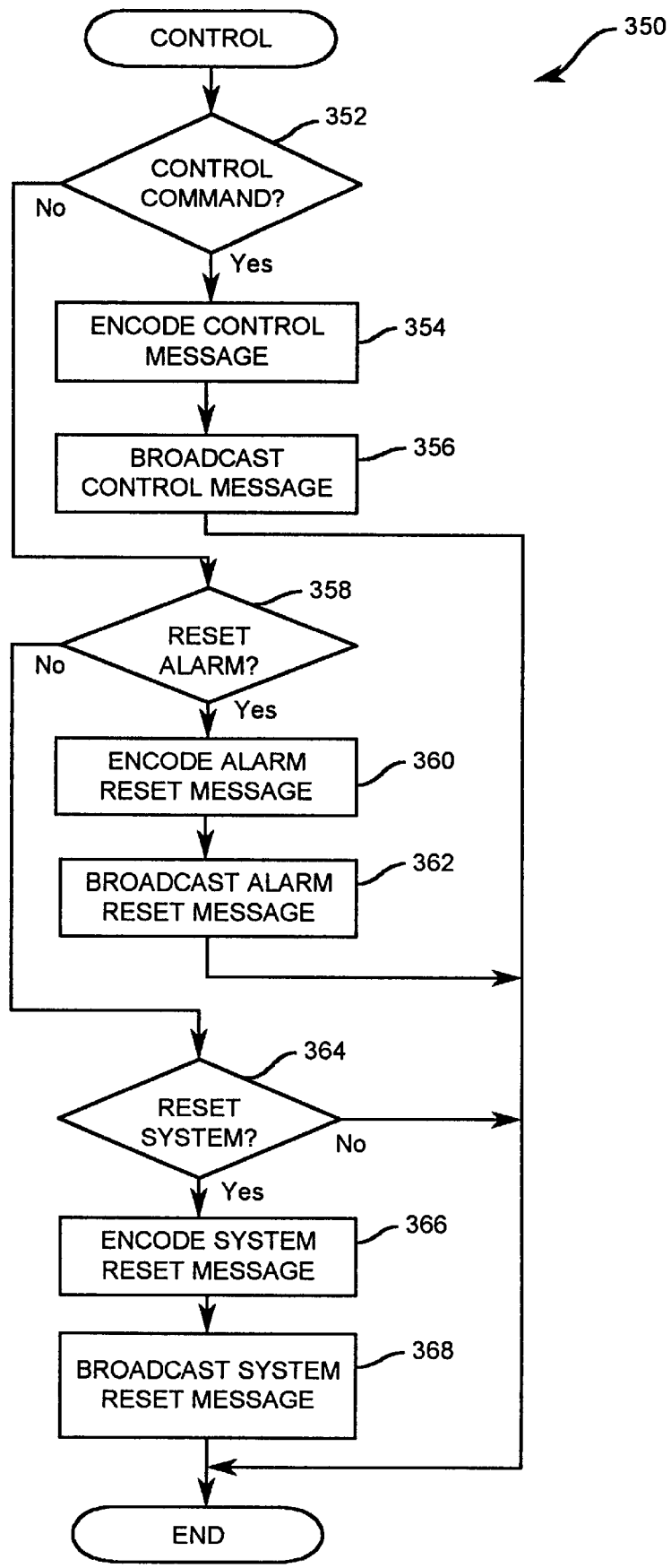

During operation of the perfusion system 10 during a medical procedure, the main controller 20 responds to various commands and other inputs entered by the operator of the system 10. FIG. 13G is a flowchart of a control command routine 350 which illustrates how the main controller 20 responds to those inputs. While FIG. 13G discloses various possible operator inputs, it should be understood that the main controller 20 could respond to other or additional operator inputs.

Referring to FIG. 13G, at step 352, if the input entered by the operator was a control command, the program branches to step 354 where a control message corresponding to the control command is encoded in a data packet, and then to step 356 where the control message is broadcast over the network 30. For example, the control message could be one of the following: 1) a new alarm limit for a particular sensing device; 2) a new mode of operation for a blood pump; 3) a new target flow value for a blood pump; 4) a new rate at which a particular sensing device should be read; 5) a pump start command; 6) a pump stop command; etc.

At step 358, if the operator requests that a particular alarm be reset, the program branches to step 360 where a corresponding alarm-reset message, which includes the logical address of the device that generated the alarm, is encoded and to step 362 where the alarm-reset message is broadcast over the network 30. At step 364, if the operator requests that the perfusion system 10 be reset, the program branches to step 366 where a corresponding system reset message is encoded and to step 362 where the system reset message is broadcast over the network 30.

Receipt of Network Messages by Main Controller

Figure 13H:
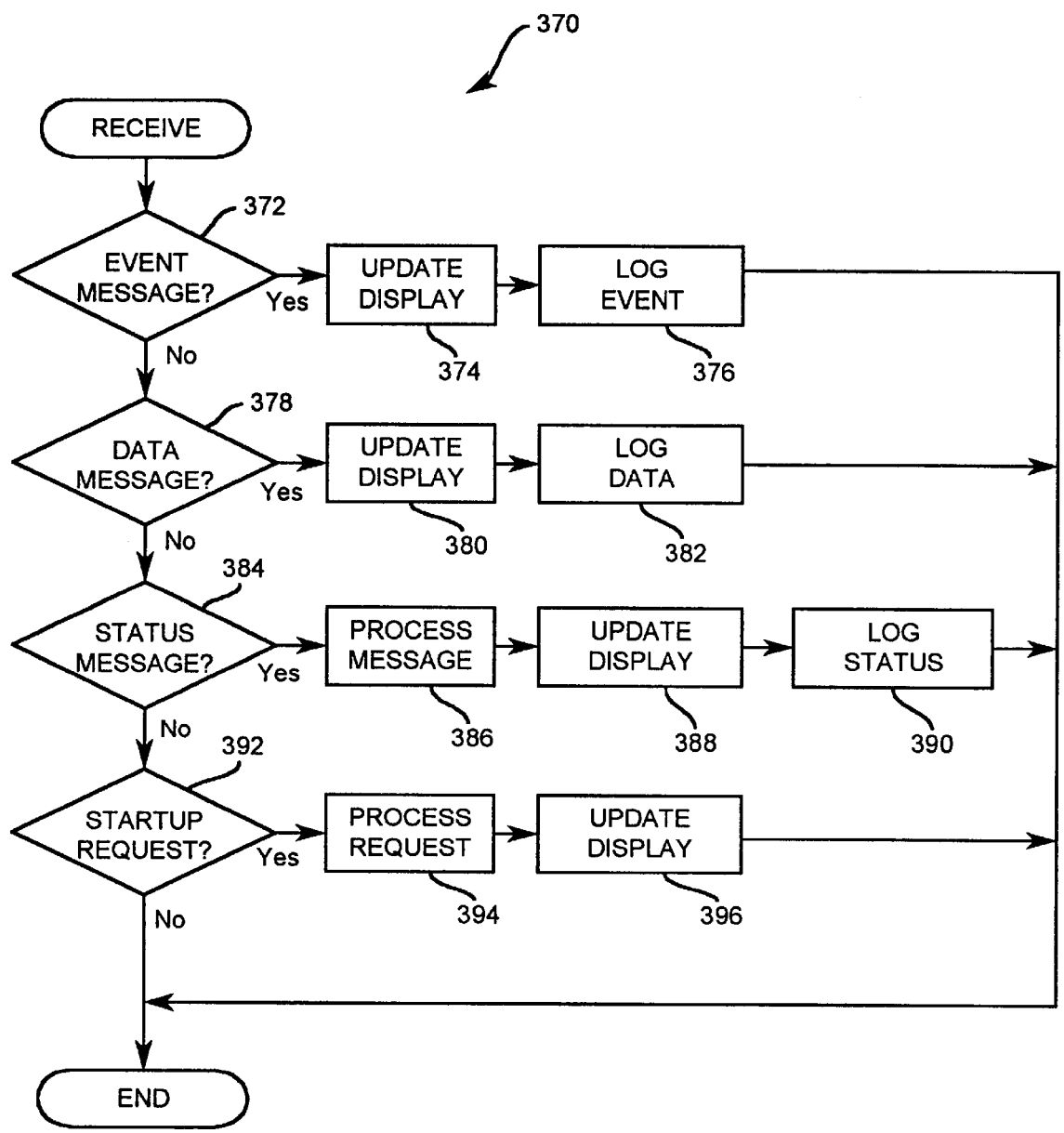

During operation, the main controller 20 receives messages of various types that are broadcast over the network 30. FIG. 13H is a flowchart of a receive routine 370 performed by the main controller 20 that illustrates actions taken by the main controller 20 in response to the receipt of various types of messages.

Referring to FIG. 13H, at step 372, if the received message corresponds to an event message, such as an alarm or other event, the program branches to step 374 where the visual display generated on the display device 114 is updated to advise the operator of that event, and the program branches to step 376 where the event is logged into an event log stored in the memory 104 of the main controller 20.

At step 378, if the received message corresponds to a data message, such as a message which includes the numeric value representing the output of a flow sensor, the program branches to step 380 where the visual display is updated, and the program branches to step 382 where the data and the device which generated the data are logged into a data log stored in the memory 104 of the main controller 20.

At step 384, if the received message is a status message, the program branches to step 386 where the status message is processed, as described above in connection with FIG. 13E. At step 388, the visual display is updated based on the status, and at step 390 the status is stored in a status log stored in memory. At step 392, if the received message is a startup request, the program branches to step 394 where the startup request is processed, as described above in connection with FIG. 13C, and at step 396, the visual display is updated.

Operation of Extender Controllers

Figure 15A:
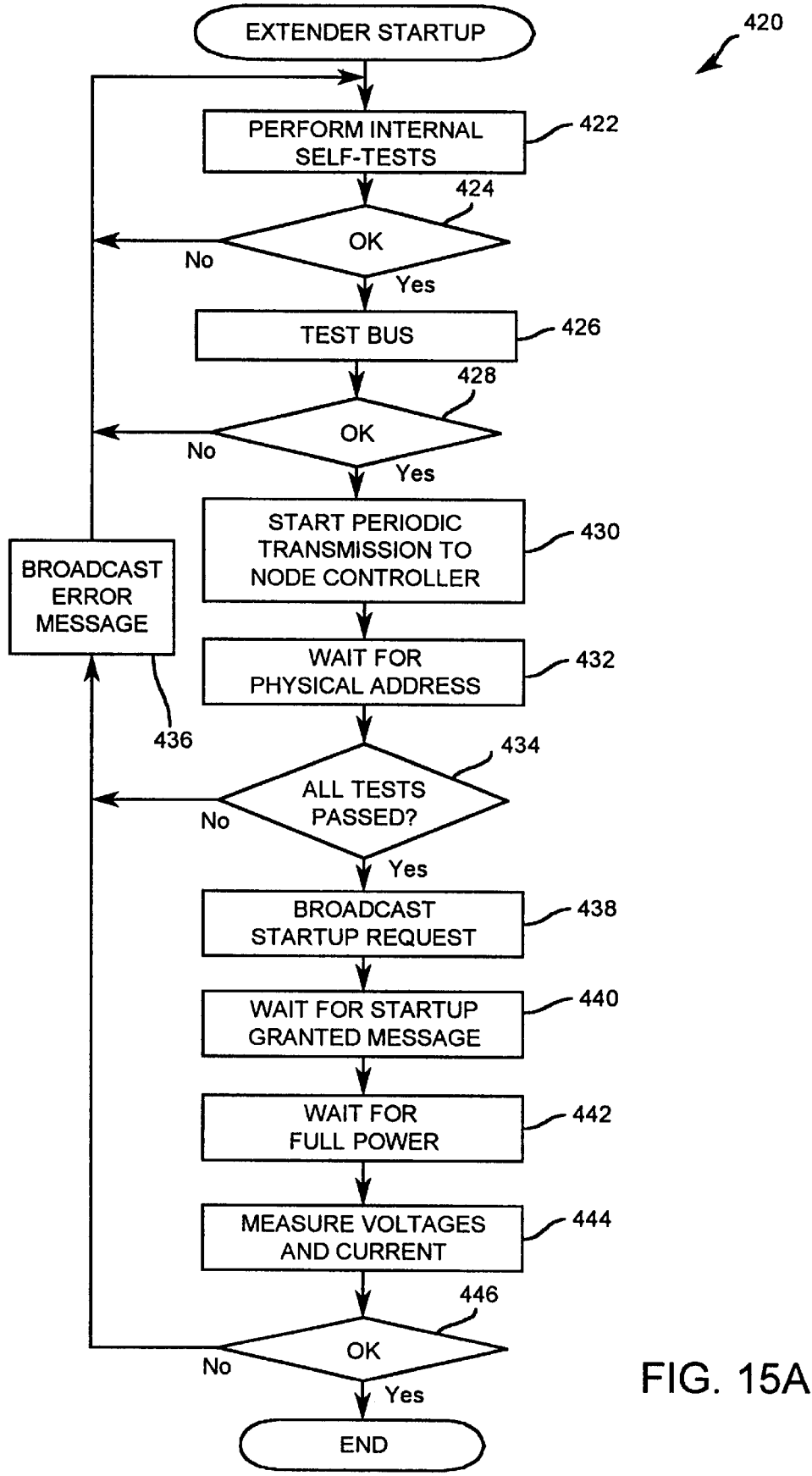
FIGS. 15A–15C are flowcharts illustrating the operation of the extender controllers shown in FIG. 1.

A basic function of the extender controllers 32 is to control the connection and disconnection of adapter pods 40 to the network 30. FIG. 15A is a flowchart of a startup routine 420 performed by the controller 130 of each extender controller 32. Referring to FIG. 15A, at step 422 the extender controller 32 performs a number of internal self-tests, such as tests of an internal RAM and an internal ROM. At step 424, if the tests were successful, the program branches to step 426 where the connection of the extender controller 32 to the network bus 30 is tested by transmitting a message onto the network bus 30 and simultaneously receiving the message from the network bus 30 as it is transmitted to determine if the message was in fact transmitted.

At step 428, if the data bus test was successful, the program branches to step 430 where the extender controller 32 starts to periodically transmit a check-in code to its parent node controller 34 via the line 133. As described below, each device (either an adapter pod 40 or an extender controller 32) must periodically transmit a check-in code to its parent node controller 34 to maintain its connection to the network 30.

At step 432, the extender controller 32 waits for its physical address to be transmitted to it from its parent node controller 34. At step 434, if not all of the tests performed at steps 422 and 426 were passed, an error message is broadcast over the network 30. The error message includes the physical address of the extender controller 32 and a binary code which specifies which test(s) were not passed.

If all tests were passed, the program branches to step 438 where a startup-request message containing the physical address of the extender controller 32 is encoded and broadcast over the network 30. At step 440, the program waits until a startup-granted message is received from the main controller 20, and then at step 442 the program waits until full power is granted to the extender controller 32 via the electrical power lines 120a, 120b of its parent node controller 34. When full power is granted, the program branches to step 444 where the extender controller 32 measures the voltages on and the current provided by the electrical power lines 120a, 120b to make sure they are within specification. At step 446, if the power measurements are not within specification, the program branches to step 436 where a message to that effect is broadcast to the main controller 20 over the network 30.

Figures 15B, 15C:
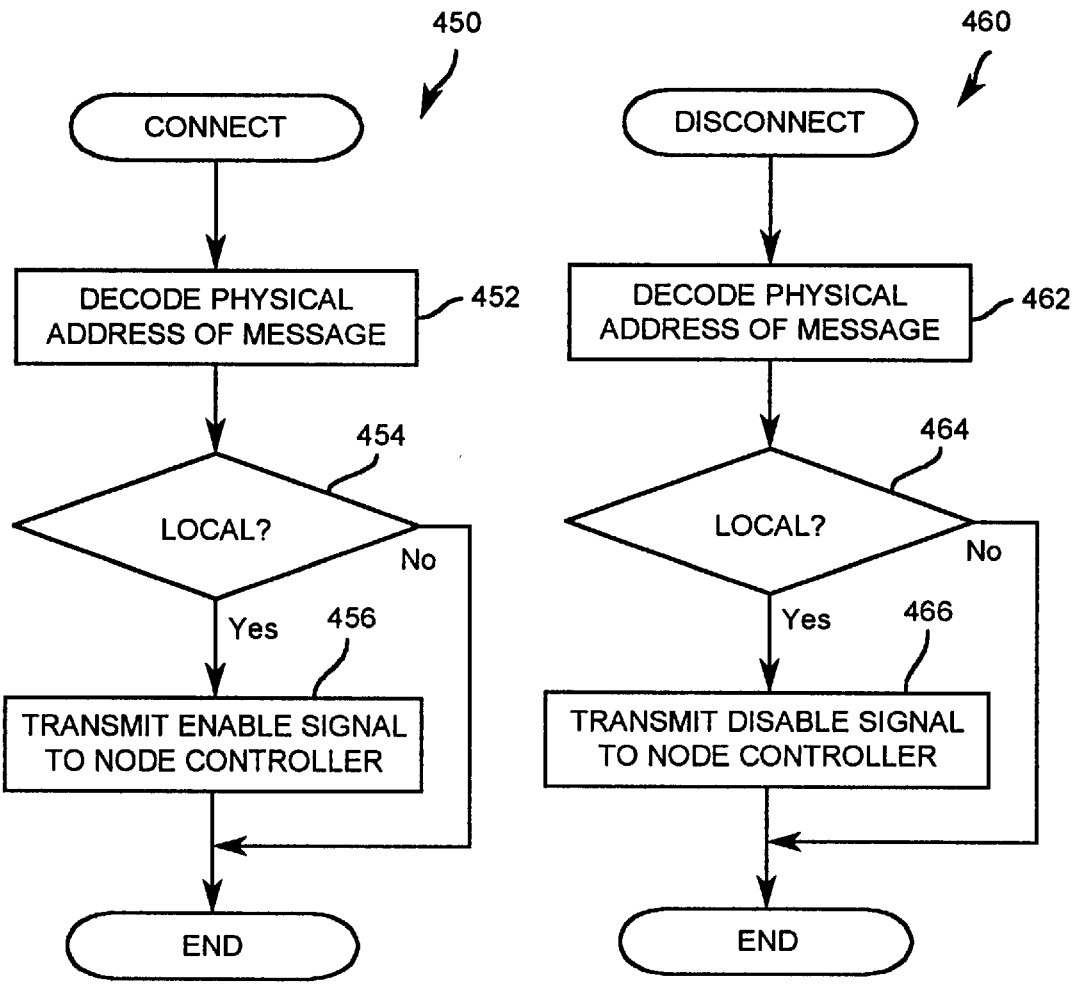

FIG. 15B is a flowchart of a connect routine 450 performed by an extender controller 32 when it receives a connect message from the main controller 20. Referring to FIG. 15B, at step 452, the connect message received from the main controller 20 is decoded to determine the physical address of the adapter pod 40 to be connected to the network 30. At step 454, the physical address is inspected to determine if the adapter pod 40 to be connected is local to the extender controller 32, meaning that the adapter pod 40 is one of the three that are connected to the extender controller 32. If the pod 40 is not local to the extender controller 32, no further action is taken and the routine 450 ends. If the pod 40 is local to the extender controller 32, the program branches to step 456 where an enable signal is transmitted via one of the lines 134 to the node controller 34 associated with the adapter pod 40 to be connected, which causes the adapter pod 40 to be connected to the network 30 in the manner described above.

When an extender controller 32 receives a disconnect message from the main controller 20, a disconnect routine 460 shown in FIG. 15C is performed by the extender controller 32. Referring to FIG. 15C, at step 462, the disconnect message received from the main controller 20 is decoded to determine the physical address of the adapter pod 40 to be disconnected to the network 30. At step 464, the physical address is inspected to determine if the adapter pod 40 to be disconnected is local to the extender controller 32. If the pod 40 is not local, no further action is taken. If the pod 40 is local, the program branches to step 466 where a disable signal is transmitted via one of the lines 134 to the node controller 34 associated with the adapter pod 40 to be disconnected, which causes the adapter pod 40 to be disconnected to the network 30.

Operation of Node Controllers

The basic function of the node controllers 34 is to connect and disconnect the adapter pods 40 (if a node controller 34 is the parent of an adapter pod 40) and the extender controllers 32 (if a node controller 34 is the parent of an extender controller 32) from the network 30. The connection or disconnection is performed pursuant to an enable or disable signal received either from the main controller 20 or from the extender controller 32 associated with the node controller 34, as described above. In addition, each node controller 34 requires its associated device 32 or 40 to periodically check-in. If the device 32 or 40 fails to check in with a proper check-in code, the node controller 34 disconnects the device 32 or 40 from the network 30.

Figure 16A:
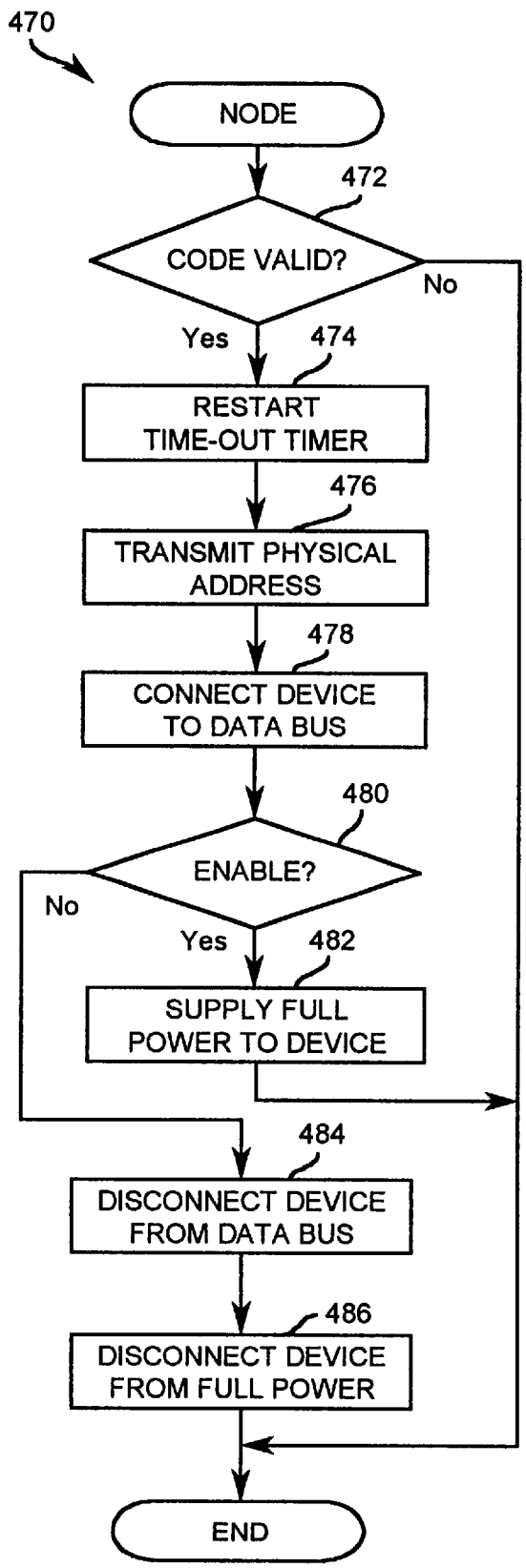
FIGS. 16A–16B are flowcharts illustrating the operation of the node controllers shown in FIG. 1.

FIG. 16A is a flowchart of a node routine 470 performed by each of the node controllers 34. The routine 470 is performed upon the receipt by the node controller 34 of a check-in code received from the associated device 32 or 40. Referring to FIG. 16A, at step 472, if the code received from the device 32 or 40 is not valid, no further action is taken and the routine ends. The check-in code may be the physical address specified by the code generator 144 (FIG. 11) of the node controller 34. To determine whether the code is valid, the node controller 34 may compare the received code to determine whether it matches a predetermined code.

If the check-in code was valid, the program branches to step 474 where a time-out timer is restarted. The time-out timer tracks the predetermined period of time within which the device 32 or 40 must transmit a valid check-in code. At step 476, the node controller 34 transmits the physical address generated by the code generator 144 to the pod 40. At step 478, the node controller 34 connects the device 32 or 40 to the data bus 152 (FIG. 11) by sending a signal to the switch 150 which causes it to close (or remain closed if it was already closed).

At step 480, if the enable signal is present on the line 134 connected to the node controller 34, the node controller 34 supplies full power to the device 32 or 40 by sending signals to the switches 154, 158 (FIG. 11) to cause them to close (or remain closed if they were already closed).

If the enable signal was not present as determined at step 480, the program branches to step 484, where the device 32 or 40 is disconnected from the data bus 152 by opening the switch 150 and to step 484 where the device 32 or 40 is disconnected from the electrical power lines 120a, 120b by opening the switches 154, 158.

Figure 16B:
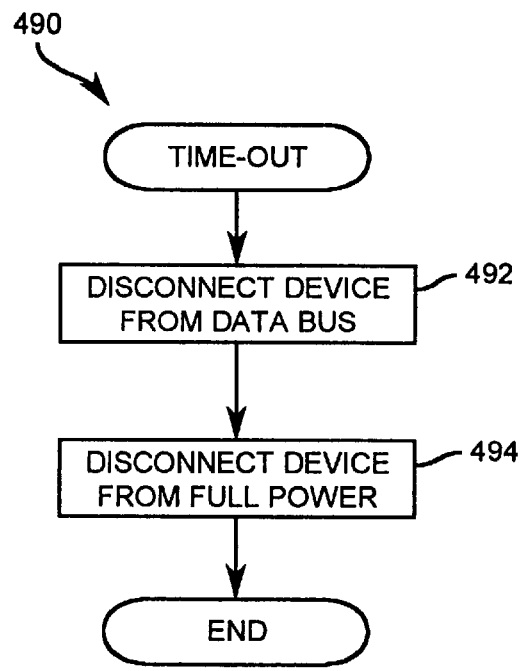

If the device 32 or 40 fails to transmit a valid check-in code to the node controller 34 within the time-out period, a time-out routine 490 shown in FIG. 16B is performed by the node controller 34. Referring to FIG. 16B, at step 492 the device 32 or 40 is disconnected from the data bus 152 by opening the switch 150, and at step 494 the device 32 or 40 is disconnected from the electrical power lines 120a, 120b by opening the switches 154, 158.

Operation of Adapter Pods

The adapter pods 40 perform a number of functions, including receiving configuration and control messages transmitted by the main controller 20, receiving sensing messages containing numeric values of sensed conditions, such as flow, and/or transmitting sensing messages over the network 30. These functions are described below.

Figure 17A:
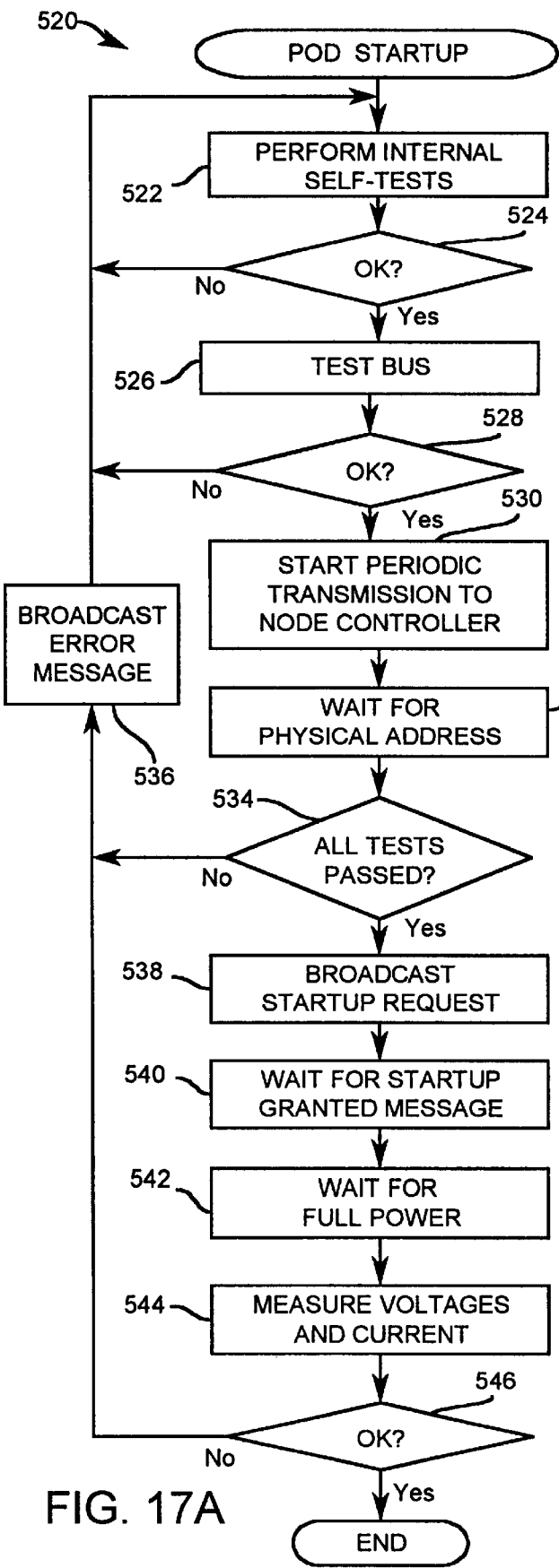
FIGS. 17A–17D are flowcharts illustrating the operation of the adapter pods shown in FIG. 1.

FIG. 17A is a flowchart of a startup routine 520 performed by the controller 180 of each adapter pod 40. Referring to FIG. 17A, at step 522 the adapter pod 40 performs a number of internal self-tests, such as tests of an internal RAM and an internal ROM. At step 524, if the tests were successful, the program branches to step 526 where the connection of the pod 40 to the data bus 152 is tested by transmitting a message onto the data bus 152 and simultaneously receiving the message from the data bus 152 as it is transmitted to determine if the message was in fact transmitted.

At step 528, if the data bus test was successful, the program branches to step 530 where the adapter pod 40 starts to periodically transmit a check-in code to its parent node controller 34 via the line 133. At step 532, the pod 40 waits for its physical address to be transmitted to it from its parent node controller 34. At step 534, if not all of the tests performed at steps 522 and 526 were passed, an error message is broadcast over the network 30. The error message includes the physical address of the pod 40 and a binary code which specifies which test(s) were not passed.

If all tests were passed, the program branches to step 538 where a startup-request message containing the physical address of the adapter pod 40 is encoded and broadcast over the network 30. At step 540, the program waits until a startup-granted message is received from the main controller 20, and then at step 542 the program waits until full power is granted to the adapter pod 40 via the electrical power lines 120a, 120b of its parent node controller 34. When full power is granted, the program branches to step 544 where the pod 40 measures the voltages on and the current provided by the electrical power lines 120a, 120b to make sure they are within specification. At step 546, if the power measurements are not within specification, the program branches to step 536 where a message to that effect is broadcast to the main controller 20 over the network 30.

Figure 17B:
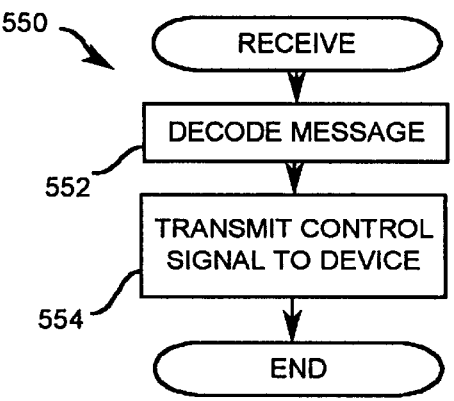

During operation, an adapter pod 40 may receive control or configuration messages from the main controller 20 over the network. FIG. 17B is a flowchart of a receive routine 550 that is performed when the adapter pod 40 receives a message. Referring to FIG. 17B, at step 552 the message is decoded to determine the control command embedded in the message, and at step 554, the pod 40 transmits a control signal (via one or more of the data lines 192 in FIG. 12) to the perfusion device 50 connected to it.

Figure 17C:
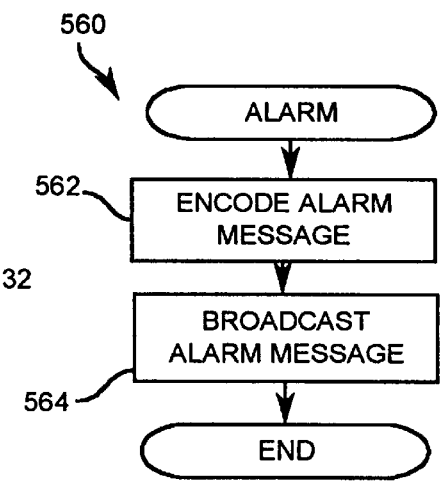

During operation, an adapter pod 40 may receive an alarm signal from the perfusion device 50 via one of the data lines 192. When such an alarm signal is received, an alarm routine 560 shown in FIG. 17C is performed by the pod 40. Referring to FIG. 17C, at step 562 an alarm message is encoded with the logical address of the perfusion device 50 that generated the alarm and the type of alarm, and at step 564 the alarm message is broadcast over the network 30 to the main controller 20.

During operation, each adapter pod 40 connected to a perfusion device 50, such as a flow sensor, which generates a sensing signal periodically reads the numeric value of the sensing signal via one of the lines 152. The time period between successive readings of the sensing signal may be specified during the configuration process as described above.

Figure 17D:
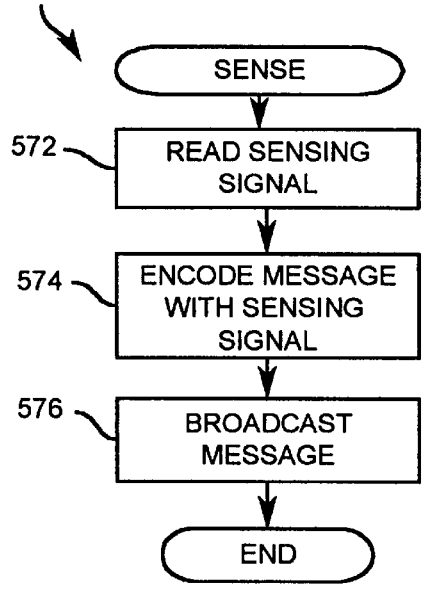

FIG. 17D is a flowchart of a sensing routine 570 that is performed when it is time to read the value of the sensing signal. Referring to FIG. 17D, at step 572 the sensing signal is read via one of the data lines 152. At step 574, the numeric value of the sensing signal is encoded in a message along with the logical address of the perfusion device 50 which generated the sensing signal. At step 576, that message is then broadcast over the network 30 to all devices connected to the network 30.

As described above, each adapter pod 40 connected to the network 30 may be provided with a message-discrimination circuit which is used to selectively receive messages from only a subset of the devices connected to the network 30. When the sensing message is broadcast at step 576, the only devices that receive it are the main controller 20 (which may receive all messages broadcast over the network 30) and the particular perfusion device 50 which is being controlled based on the value of the sensing signal encoded in the sensing message.

It should be understood that the adapter pods may be provided with additional functionality not described above. Also, instead of having electrical power being distributed over the network from a single power source provided in the main controller 20, electrical power could be distributed from a plurality of power sources, for example, from one power source provided in each of the network extenders.

Since numerous additional modifications and alternative embodiments of the invention will be apparent to those skilled in the art in view of the foregoing description, the above description is to be construed as illustrative only, and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. A medical perfusion system for use in connection with the medical treatment of a patient, comprising:

a first blood pump adapted to pump blood through a first conduit fluidly connected to the patient;

a second blood pump adapted to pump blood through a second conduit fluidly connected to the patient;

a first sensor for sensing a first condition relating to the pumping of blood through said first conduit, said first sensor generating a sensing signal relating to said first second condition;

a second sensor for sensing a condition relating to the pumping of blood through said second conduit, said second sensor generating a sensing signal relating to said second condition;

a data communications network for operatively interconnecting said blood pumps and said sensors, said data communications network having a plurality of network connectors, each of said network connectors having an identical connector configuration;

a first adapter pod having a common connector and a device connector, said common connector being adapted to be coupled to one of said network connectors and said device connector being adapted to be coupled to said first pump;

a second adapter pod having a common connector and a device connector, said common connector of said second adapter pod being adapted to be coupled to one of said network connectors and said device connector of said second adapter pod being adapted to be coupled to said second pump;

a third adapter pod having a common connector and a device connector, said common connector of said third adapter pod being adapted to be coupled to one of said network connectors and said device connector of said third adapter pod being adapted to be coupled to said first sensor;

a fourth adapter pod having a common connector and a device connector, said common connector of said fourth adapter pod being adapted to be coupled to one of said network connectors and said device connector of said fourth adapter pod being adapted to be coupled to said second sensor, said device connector of said fourth adapter pod having a different structure than said device connector of said first adapter pod;

means for transmitting messages in the form of digital data packets among said first and second blood pumps and said first and second sensors over said data communications network; and a controller operatively coupled to said blood pumps and said sensors via said data communications network, said controller having an input device for accepting pump control commands relating to said first and second blood pumps from an operator.

2. A system as defined in claim 1 wherein said device connector of said fourth adapter pod has a first number of signal lines and wherein said common connector of said fourth adapter pod has a second number of signal lines different than said first number.

3. A system as defined in claim 1 wherein said means for transmitting messages comprises:

means for generating a message containing a control command for one of said pumps; and means for generating a message containing data relating to one of said first and second conditions.

4. A system as defined in claim 1 wherein each of said adapter pods comprises means for generating a message in the form of a digital data packet.

5. A system as defined in claim 1 wherein said controller includes a plurality of network connectors and wherein said data communications network includes a network extender comprising:

a network connector adapted to be operatively coupled to one of said network connectors of said controller;

a plurality of extender connectors adapted to be connected to said common connectors of said adapter pods; and a data bus electrically interconnecting said network connector of said network extender with each of said extender connectors.

6. A system as defined in claim 1 wherein said controller additionally comprises a network controller for controlling transmission of said messages over said data communications network.

7. A medical perfusion system for use in connection with the medical treatment of a patient, comprising:

a first type of perfusion device, said first type of perfusion device comprising a blood pump being adapted to pump blood through a fluid conduit connected to the patient;

a second type of perfusion device, said second type of perfusion device being adapted to sense a condition relating to the pumping of blood through said fluid conduit, said second type of perfusion device generating a sensing signal relating to said condition;

a data communications network for operatively interconnecting said first type of perfusion device and said second type of perfusion device, said data communications network having a plurality of network connectors, each of said network connectors having an identical connector configuration;

a first adapter pod having a common connector and a device connector, said common connector being adapted to be coupled to one of said network connectors and said device connector being adapted to be coupled to said blood pump;

a second adapter pod having a common connector and a device connector, said common connector of said second adapter pod being adapted to be coupled to one of said network connectors and said device connector of said second adapter pod being adapted to be coupled to said second type of perfusion device, said device connector of said second adapter pod having a different structure than said device connector of said first adapter pod;

means for transmitting messages in the form of digital data packets among said perfusion devices over said data communications network; and a controller operatively coupled to said perfusion devices via said data communications network, said controller having an input device for accepting pump control commands relating to said blood pump from an operator.

8. A system as defined in claim 7 wherein said device connector of said first adapter pod has a first number of signal lines and wherein said common connector of said first adapter pod has a second number of signal lines different than said first number.

9. A system as defined in claim 7 wherein said means for transmitting messages comprises:

means for generating a message containing a control command for said pump; and means for generating a message containing data relating to said condition.

10. A system as defined in claim 7 wherein each of said adapter pods comprises means for generating a message in the form of a digital data packet.

11. A system as defined in claim 7 wherein said controller includes a plurality of network connectors and wherein said data communications network includes a network extender comprising:

a network connector adapted to be operatively coupled to one of said network connectors of said controller;

a plurality of extender connectors adapted to be connected to said common connectors of said adapter pods; and a data bus electrically interconnecting said network connector of said network extender with each of said extender connectors.

12. A system as defined in claim 7 wherein said controller additionally comprises a network controller for controlling transmission of said messages over said data communications network.

13. A medical perfusion system for use in connection with the medical treatment of a patient, comprising:

a first type of perfusion device, said first type of perfusion device comprising a blood pump being adapted to pump blood through a fluid conduit connected to the patient;

a second type of perfusion device, said second type of perfusion device being adapted to sense a condition relating to the pumping of blood through said fluid conduit, said second type of perfusion device generating a sensing signal relating to said condition;

a data communications network for operatively interconnecting said first type of perfusion device and said second type of perfusion device;

means for transmitting messages in the form of digital data packets among said perfusion devices over said data communications network; and a controller operatively coupled to said perfusion devices via said data communications network, said controller having an input device for accepting pump control commands relating to said blood pump from an operator, wherein said data communications network has a plurality of network connectors and a network extender comprising:

a network connector adapted to be operatively coupled to one of said network connectors of said controller;

a plurality of extender connectors; and a data bus electrically interconnecting said network connector of said network extender with each of said extender connectors.

14. A system as defined in claim 13 wherein said means for transmitting messages comprises:

means for generating a message containing a control command for said pump; and means for generating a message containing data relating to said condition.

15. A system as defined in claim 13 wherein said controller additionally comprises a network controller for controlling transmission of said messages over said data communications network.

* * * * *

UNITED STATES PATENT AND TRADEMARK OFFICE
CERTIFICATE OF CORRECTION

PATENT NO.: 5,813,972

DATED: September 29, 1998

INVENTOR(S): Richard A. Nazarian, Dirk R. Smith, James R. Watts, Timothy J. Kriewall and Richard A. Griewski It is certified that error appears in the above-identified patent and that said Letters Patent is hereby corrected as shown below:

Col. 18, line 3, before "condition" insert --second--.

Signed and Sealed this

Third Day of April, 2001

Attest:

NICHOLAS P. GODICI

Attesting Officer     Acting Director of the United States Patent and Trademark Office